United States Patent
Turner et al.

(10) Patent No.: US 12,303,622 B2
(45) Date of Patent: May 20, 2025

(54) METHOD OF DELIVERING A VOLATILE COMPOSITION INTO THE AIR

(71) Applicant: The Procter & Gamble Company, Cincinnati, OH (US)

(72) Inventors: David Turner, Cincinnati, OH (US); Leslie Roselle Deaton, Alexandria, KY (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 18/812,394

(22) Filed: Aug. 22, 2024

(65) Prior Publication Data
US 2024/0408260 A1    Dec. 12, 2024

Related U.S. Application Data

(63) Continuation of application No. 18/529,589, filed on Dec. 5, 2023, which is a continuation of application
(Continued)

(51) Int. Cl.
*A61L 9/03* (2006.01)
*A61L 9/12* (2006.01)

(52) U.S. Cl.
CPC ............ *A61L 9/037* (2013.01); *A61L 9/032* (2013.01); *A61L 9/035* (2013.01); *A61L 9/122* (2013.01);
(Continued)

(58) Field of Classification Search
CPC . A61L 9/048; A61L 9/12; A61L 9/122; A61L 9/125; A61L 9/127; A61L 2209/11;
(Continued)

(56) References Cited

U.S. PATENT DOCUMENTS 5,175,791 A    12/1992   Muderlak et al.
5,402,517 A     3/1995   Gillett et al.
(Continued)

FOREIGN PATENT DOCUMENTS

CN       1642583 A    7/2005
CN     102648007 A    8/2012
(Continued)

OTHER PUBLICATIONS

ES2619153 (Year: 2024).*
(Continued)

*Primary Examiner* — Steven W Crabb
*Assistant Examiner* — Frederick F Calvetti
(74) *Attorney, Agent, or Firm* — Carolyn S. Powell; Elizabeth A. Conklin

(57) ABSTRACT

A volatile composition dispenser and methods of volatilizing a volatile composition in the air are provided. The volatile composition dispenser includes one or more reservoirs, with each reservoir containing a volatile composition. Each reservoir has one or more delivery engines disposed in fluid communication with the volatile composition in the reservoir. Each delivery engine is in fluid communication with an evaporative surface. One or more evaporative assistance elements are disposed adjacent to the evaporative surface(s). A method of volatilizing the volatile composition(s) includes operating the evaporative assistance elements with varying energy over a total emission program, including energy boost periods, and extended emission periods of decreased or maintained energy.

26 Claims, 17 Drawing Sheets

Related U.S. Application Data

No. 16/246,570, filed on Jan. 14, 2019, now Pat. No. 11,896,743.

(60) Provisional application No. 62/618,644, filed on Jan. 18, 2018.

(52) U.S. Cl.
CPC ...... *A61L 2209/11* (2013.01); *A61L 2209/135* (2013.01)

(58) Field of Classification Search
CPC .......... A61L 9/037; A61L 9/032; A61L 9/035; A61L 2209/135
See application file for complete search history.

(56) References Cited

U.S. PATENT DOCUMENTS

| | | | |
|---|---|---|---|
| 6,478,440 B1 | 11/2002 | Jaworski | |
| 6,712,287 B1 | 3/2004 | Le et al. | |
| 6,790,408 B2 | 9/2004 | Whitby | |
| 6,792,199 B2 | 9/2004 | Levine et al. | |
| 6,996,335 B2 | 2/2006 | Zobele | |
| 7,011,795 B2 | 3/2006 | Thompson et al. | |
| 7,223,361 B2 | 5/2007 | Kvietok | |
| 7,263,282 B2 | 8/2007 | Meyer | |
| 7,493,028 B2 | 2/2009 | Dewitt et al. | |
| 7,622,073 B2 | 11/2009 | Schramm et al. | |
| 7,722,807 B2 | 5/2010 | Keller, Jr. | |
| 7,887,759 B2 | 2/2011 | Triplett | |
| 7,930,068 B2 | 4/2011 | Robert et al. | |
| 7,962,017 B2 | 6/2011 | Viera | |
| 7,981,367 B2 | 7/2011 | Kvietok et al. | |
| 8,016,207 B2 | 9/2011 | Kvietok et al. | |
| 8,061,628 B1 | 11/2011 | Kvietok et al. | |
| 8,119,064 B2 | 2/2012 | Woo et al. | |
| 8,197,762 B2* | 6/2012 | Gasper | A61L 9/122 221/9 |
| 8,210,448 B2 | 7/2012 | Kvietok et al. | |
| 8,255,089 B2 | 8/2012 | Luc et al. | |
| 8,293,172 B2 | 10/2012 | Gasper | |
| 8,320,751 B2* | 11/2012 | Porchia | A61L 9/032 392/386 |
| 8,349,251 B2 | 1/2013 | Woo et al. | |
| 8,459,499 B2 | 6/2013 | Sipinski | |
| 8,565,926 B2 | 10/2013 | Luc et al. | |
| 8,651,395 B2 | 2/2014 | Kvietok et al. | |
| 8,721,962 B2* | 5/2014 | Woo | B60H 3/0007 422/123 |
| 8,855,827 B2 | 10/2014 | Weening et al. | |
| 8,868,245 B2 | 10/2014 | Luc et al. | |
| 8,891,947 B2* | 11/2014 | Neumann | A61L 9/035 392/386 |
| 8,983,279 B2* | 3/2015 | Adair | H05B 1/0225 392/395 |
| 9,101,676 B2 | 8/2015 | Hoppe et al. | |
| 9,446,162 B2 | 9/2016 | Chandler et al. | |
| 9,460,404 B2 | 10/2016 | Chandler et al. | |
| 9,499,770 B2 | 11/2016 | Morgan et al. | |
| 9,669,125 B2 | 6/2017 | Gasper | |
| 9,715,223 B2 | 7/2017 | Chandler et al. | |
| 9,737,627 B2* | 8/2017 | Turner | A61L 9/01 |
| 9,789,219 B2 | 10/2017 | Kelly et al. | |
| 9,808,812 B2* | 11/2017 | Gruenbacher | B05B 17/0684 |
| 10,639,448 B2 | 5/2020 | Leon | |
| 10,764,963 B2* | 9/2020 | Davis | A61L 9/037 |
| 11,083,813 B2 | 8/2021 | Avidor | |
| 11,246,954 B2 | 2/2022 | Fischer | |
| 11,896,743 B2 | 2/2024 | Turner | |
| 2004/0028551 A1* | 2/2004 | Kvietok | A61L 9/122 422/123 |
| 2004/0033067 A1 | 2/2004 | He | |
| 2004/0033171 A1* | 2/2004 | Kvietok | A61L 9/035 422/123 |
| 2004/0265164 A1 | 12/2004 | Woo | |
| 2006/0076429 A1* | 4/2006 | Kvietok | A61L 9/04 239/6 |
| 2006/0175426 A1 | 8/2006 | Schramm et al. | |
| 2006/0193611 A1 | 8/2006 | Ruiz et al. | |
| 2007/0166185 A1 | 7/2007 | Bartels | |
| 2007/0172382 A1* | 7/2007 | Uchiyama | A61L 9/14 422/5 |
| 2008/0014125 A1 | 1/2008 | He et al. | |
| 2008/0069725 A1* | 3/2008 | Kvietok | A61L 9/037 422/4 |
| 2008/0191370 A1* | 8/2008 | Pankhurst | A61L 9/035 261/99 |
| 2009/0162253 A1* | 6/2009 | Porchia | A61L 9/02 422/124 |
| 2009/0224064 A1* | 9/2009 | Brodbeck | F22B 27/00 122/366 |
| 2010/0078498 A1* | 4/2010 | Gasper | A61L 9/02 239/6 |
| 2010/0294852 A1* | 11/2010 | Banco | A61L 9/037 239/6 |
| 2011/0032992 A1* | 2/2011 | Cote | H04N 19/513 375/E7.125 |
| 2011/0049259 A1* | 3/2011 | Beland | A61L 9/037 239/7 |
| 2011/0068190 A1 | 3/2011 | Gasper | |
| 2011/0132992 A1* | 6/2011 | Hoppe | A61L 9/02 239/34 |
| 2012/0097753 A1 | 4/2012 | Kelly | |
| 2013/0134233 A1 | 5/2013 | Woo | |
| 2014/0037273 A1 | 2/2014 | Jaworski et al. | |
| 2014/0064713 A1* | 3/2014 | Niemiec | A61L 9/035 392/387 |
| 2014/0369895 A1 | 12/2014 | Turner | |
| 2015/0367014 A1 | 12/2015 | Gruenbacher | |
| 2015/0367042 A1* | 12/2015 | Merckle | A61B 18/14 606/41 |
| 2016/0353858 A1 | 12/2016 | Chandler et al. | |
| 2016/0367715 A1* | 12/2016 | Turner | A61L 9/122 |
| 2017/0049920 A1 | 2/2017 | Weening et al. | |
| 2018/0093006 A1 | 4/2018 | Kelly et al. | |
| 2019/0070329 A1 | 3/2019 | Gruenbacher | |
| 2019/0216967 A1* | 7/2019 | Turner | A61L 9/037 |
| 2019/0231918 A1 | 8/2019 | Rubin | |
| 2020/0390927 A1* | 12/2020 | Fischer | A61L 9/122 |
| 2023/0061458 A1 | 3/2023 | Gruenbacher et al. | |
| 2024/0108775 A1* | 4/2024 | Turner | A61L 9/032 |

FOREIGN PATENT DOCUMENTS

| | | | |
|---|---|---|---|
| CN | 105188777 A | | 12/2015 |
| EP | 1767227 A2 | | 3/2007 |
| ES | 2619153 | * | 6/2017 |
| JP | 2006522617 A | | 10/2006 |
| WO | 2007079046 A1 | | 7/2007 |
| WO | 2009117639 A3 | | 3/2010 |
| WO | 2010036377 A1 | | 4/2010 |

OTHER PUBLICATIONS

PCT Search Report and Written Opinion for PCT/US2019/013427 dated Jul. 3, 2019, 14 pages.
All Office Actions, U.S. Appl. No. 16/246,570, filed Jan. 14, 2019.
All Office Actions; U.S. Appl. No. 18/529,589, filed Dec. 5, 2023.

* cited by examiner

METHOD OF DELIVERING A VOLATILE COMPOSITION INTO THE AIR

FIELD

The present invention is directed to a method of delivering a volatile composition into the air using varying energy levels for long-lasting noticeability of the volatile composition.

BACKGROUND

Volatile composition dispensers exist for delivering various volatile compositions, such as freshening compositions, into the air. Such volatile composition dispensers may, for example, take the form of a wick-based electrical dispenser having one or more heaters to assist with volatizing the volatile composition into the air. Consumers desire for the volatile composition dispenser to provide noticeable intensity of the volatile composition over a period of weeks or months. However, noticeability can be impacted by habituation and/or decreasing evaporation rate of the volatile composition from the volatile composition dispenser. Attempts have been made to increase noticeability, but these attempts can result in faster evaporation of the volatile composition. Thus, there remains a need to deliver a volatile composition dispenser that provides long-lasting consumer noticeability.

SUMMARY

Aspects of the present invention include the following combinations:

A. A method of dispensing a volatile composition, the method comprising the steps of:
  providing a volatile composition dispenser, the volatile composition dispenser comprising a reservoir comprising the volatile composition, a delivery engine in fluid communication with the reservoir, an evaporative surface in fluid communication with the delivery engine, and an evaporative assistance element adjacent at least a portion of the evaporative surface, wherein the evaporative assistance element defines a maximum power output;
  starting a total emission program for the volatile composition dispenser;
  increasing the energy applied by the evaporative assistance element to a first energy in a first energy boost period, wherein the first energy is the highest energy within the first 24 hours of starting the total emission program;
  operating the evaporative assistance element below the first energy over a first extended emission period following the step of increasing the energy applied to the evaporative assistance element;
  increasing the energy applied by the evaporative assistance element to a second energy in a second energy boost period, wherein the second energy is less than the first energy;
  operating the evaporative assistance element at or below the second energy over a second extended emission period, wherein the length of the second energy boost period is no more than half of the length of the second extended emission period; and
  increasing the energy applied by the evaporative assistance element to a third energy in a third energy boost period, wherein the third energy is greater than the first energy.

B. The method according to Paragraph A, wherein the second energy boost period is no more than one-third of the length of the second extended emission period.

C. The method according to Paragraph A or Paragraph B, wherein the steps of applying the first, second, and third energy boosts further comprises increasing the power to the evaporative assistance element relative to the maximum power output.

D. The method according to any of Paragraphs A through C, wherein the evaporative assistance element comprises a heater.

E. The method according to any of Paragraphs A through D, wherein the step of increasing the energy applied by the evaporative assistance element to the second energy in a second energy boost period further comprises increasing the energy applied by the evaporative assistance element by at least 5% to the second energy in a second energy boost period.

F. The method according to any of Paragraphs A through E, wherein the volatile composition dispenser further comprises a plurality of user-controlled power settings.

G. The method according to any of Paragraphs A through F, wherein the reservoir is a first reservoir, wherein the volatile composition is a first volatile composition, wherein the delivery engine is a first delivery engine, wherein the evaporative surface is a first evaporative surface, and wherein the volatile composition dispenser further comprises a second reservoir comprising a second volatile composition, a second delivery engine in fluid communication with the second reservoir, a second evaporative surface in fluid communication with the second delivery engine, and a second evaporative assistance element that applies energy to the second evaporative surface.

H. The method according to Paragraph G, wherein the second extended emission period comprises a plurality of discrete emission periods, wherein each of the plurality of discrete emission periods are separated by periods where the first evaporative assistance element is turned OFF or the power is reduced to less than 20% of the maximum power output, wherein the method further comprises the steps of:
  turning OFF the first evaporative assistance element after a first discrete emission period; and
  turning ON the second evaporative assistance element to apply energy to the second evaporative surface simultaneously or after a gap in time after the first evaporative assistance element is turned OFF.

I. The method according to Paragraph G or Paragraph H, wherein the length of time of each of the plurality of discrete emission periods are randomly selected from a random number generator or a picklist.

J. The method according to any of Paragraphs A through I, wherein the step of increasing the energy applied by the evaporative assistance element to the third energy in a third energy boost period further comprises increasing the energy applied by the evaporative assistance element by at least 200% to the third energy in the third energy boost period.

K. The method according to any of Paragraphs A through J, wherein the first energy is a temperature in the range of about 40° C. to about 80° C., wherein the second energy is a temperature in the range of about 50° C. to about 90° C., wherein the third energy is a temperature in the range of about 60° C. to about 100° C.

L. A method of dispensing a volatile composition, the method comprising the steps of:
  providing a volatile composition dispenser, the volatile composition dispenser comprising a first reservoir containing a first composition and a second reservoir containing a second composition, a first delivery engine in fluid communication with the first reservoir, a second delivery engine in fluid communication with the second reservoir, a first evaporative surface in fluid communication with the first delivery engine, a second evaporative surface in fluid communication with the second delivery engine, a first evaporative assistance element adjacent at least a portion of the first evaporative surface, and a second evaporative assistance element adjacent at least a portion of the second evaporative surface, wherein the first and second delivery engines comprise a wick, and wherein the first and second evaporative assistance elements comprise a heater, wherein the first and second evaporative assistance elements each define a maximum power output;

starting a total emission program for the volatile composition dispenser, wherein the total emission program includes the steps of:

increasing the energy applied by the first or second evaporative assistance element to a first energy in a first energy boost period, wherein the first energy is the highest energy within the first 24 hours of starting the total emission program;

operating the first or second evaporative assistance element below the first energy over a first extended emission period following the step of increasing the energy applied to the first or second evaporative assistance element;

increasing the energy applied by the first or second evaporative assistance element to a second energy in a second energy boost period, wherein the second energy is less than the first energy;

operating the first or second evaporative assistance element at or below the second energy over a second extended emission period, wherein the length of the second energy boost period is no more than half of the length of the second extended emission period; and increasing the energy applied by the first or second evaporative assistance element to a third energy in a third energy boost period, wherein the third energy is greater than the first energy;

alternating operation of the first and second evaporative assistance elements in a plurality of discrete emission periods over the total emission program, wherein the discrete emission periods for the first evaporative assistance element are separated by periods when the first evaporative assistance element is OFF and the second evaporative assistance element is ON, and wherein the discrete emission periods for the second evaporative assistance element are separated by periods when the second evaporative assistance element is OFF and the first evaporative assistance element is ON.

M. The method according to Paragraph L further comprising the step of turning OFF operation of the first and second evaporative assistance elements simultaneously to cause a gap in emission of the volatile composition.

N. The method according to any of Paragraphs L through M, wherein the length of time of each of the plurality of discrete emission periods are randomly selected from a random number generator or a picklist.

O. A method of dispensing a volatile composition, the method comprising the steps of:

providing a volatile composition dispenser, the volatile composition dispenser comprising a reservoir comprising the volatile composition, a delivery engine in fluid communication with the reservoir, an evaporative surface in fluid communication with the delivery engine, and an evaporative assistance element adjacent at least a portion of the evaporative surface, wherein the evaporative assistance element defines a maximum power output;

starting a total emission program for the volatile composition dispenser;

increasing the evaporation rate of the volatile composition from the evaporative surface to a first evaporation rate in a first energy boost period, wherein the first evaporation rate is the highest evaporation rate within the first 24 hours of starting the total emission program;

evaporating the volatile composition from the evaporative surface below the first evaporation rate over a first extended emission period following the step of increasing the evaporation rate to a first evaporation rate;

increasing the evaporation rate to a second evaporation rate in a second energy boost period;

evaporating the volatile composition from the evaporative surface below the second evaporation rate over a second extended emission period following the step of increasing the evaporation rate to a second evaporation rate, wherein the length of the second energy boost period is no more than half of the length of the second extended emission period; and increasing the evaporation rate to a third evaporation rate in a third energy boost period, wherein the evaporation rate is between 15 mg/hour and 50 mg/hour over the total emission program.

P. The method according to Paragraph O, wherein the second energy boost period is no more than one-third of the length of the second extended emission period.

Q. The method according to Paragraph O or Paragraph P, wherein the evaporative assistance element comprises a heater, and wherein the delivery engine comprises a wick.

R. The method according to any of Paragraphs O through Q, wherein the step of increasing the evaporation rate in a second energy boost period further comprises increasing the evaporation rate by at least 5% to the second evaporation rate in the second energy boost period.

S. The method according to any of Paragraphs O through R, wherein the reservoir is a first reservoir, wherein the volatile composition is a first volatile composition, wherein the delivery engine is a first delivery engine, wherein the evaporative surface is a first evaporative surface, and wherein the volatile composition dispenser further comprises a second reservoir comprising a second volatile composition, a second delivery engine in fluid communication with the second reservoir, a second evaporative surface in fluid communication with the second delivery engine, and a second evaporative assistance element that applies energy to the second evaporative surface.

DETAILED DESCRIPTION

Figure 1:
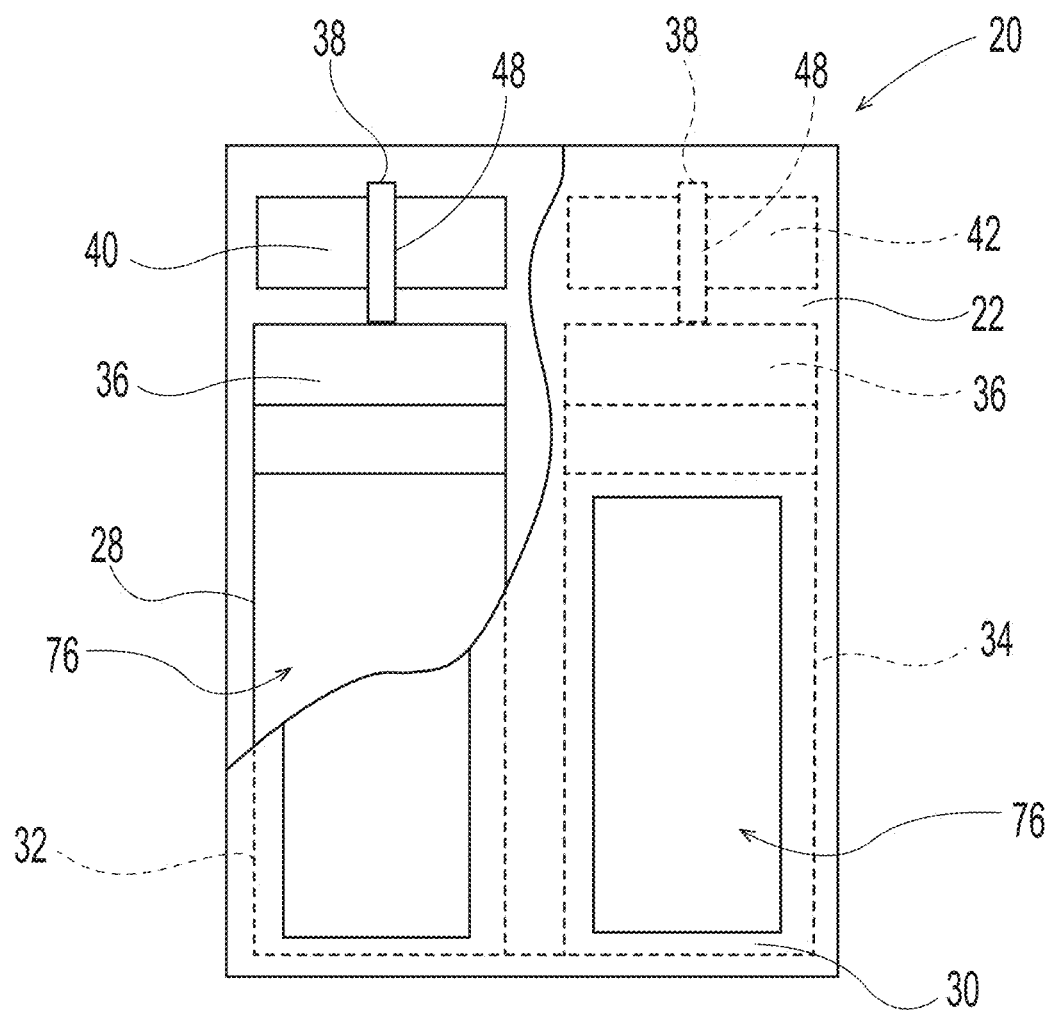
FIG. 1 is a partially fragmented schematic front view showing a volatile composition dispenser comprising two delivery engines in the form of wicks.

The present invention is directed to a volatile composition dispenser and method of delivering a volatile composition into the air using a volatile composition dispenser. The volatile composition dispenser is configured to deliver a volatile composition into the air with increased noticeability over the life of the volatile composition contained within a reservoir. It has been found that varying the energy applied to the volatile composition over a total emission cycle can affect the consumer noticeability of the volatile composition over time. In particular, an initial energy boost period applied to the volatile composition, followed by a decrease in energy for an extended emission period, with successive energy boosts and variation in energy over a period results in improved noticeability of the volatile composition by the user.

The term "volatile compositions" as used herein, refers to a material that comprises a vaporizable material. The term "volatile compositions," thus includes (but is not limited to) compositions that are comprised entirely of a single volatile material. The terms "volatile materials," "aroma," "fragrance," and "scents," as used herein, include, but are not limited to pleasant or savory smells, and, thus, also encompass materials that function as insecticides, air fresheners, deodorants, aromacology, aromatherapy, insecticides, or any other material that acts to condition, modify, or otherwise charge the atmosphere or to modify the environment. It should be understood that certain volatile compositions including, but not limited to perfumes, aromatic materials, and scented materials, will often comprise one or more volatile materials (which may form a unique and/or discrete unit comprised of a collection of volatile materials). It should be understood that the term "volatile composition" refers to compositions that have at least one volatile component, and it is not necessary for all of the component materials of the volatile composition to be volatile. The volatile compositions described herein may, thus, also have non-volatile components. It should also be understood that when the volatile compositions are described herein as being "emitted," this refers to the volatilization of the volatile components thereof, and does not require that the non-volatile components thereof be emitted. The volatile compositions of interest herein can be in any suitable form including, but not limited to, solids, liquids, gels, encapsulates, and combinations thereof.

It is contemplated that the volatile composition dispenser may be configured for use in a variety of applications to deliver the volatile composition to the air and/or ultimately to a surface. The volatile composition dispenser may be configured in various ways.

For example, the volatile composition dispenser may be configured as an electrical wall plug or battery-operated volatile composition dispenser having housing, a reservoir containing a volatile composition, a delivery engine that is used to transport the volatile composition to an evaporative surface, and an evaporative assistance element to assist with the volatilization of the volatile composition from the evaporative surface. The evaporative assistance element may be placed adjacent to the evaporative surface.

The reservoirs can comprise any suitable type of container and can be made of any suitable material. Suitable materials for the reservoirs include, but are not limited to glass and plastic. The reservoirs can comprise any type of container that is suitable for holding volatile compositions. The reservoirs may be part of the housing, or they may be separate components that are removably joined to a portion of the volatile composition dispenser such as the housing. It is also possible for a single reservoir to hold more than one type of volatile material. Such a reservoir could, for instance, have two or more compartments for volatile materials.

The delivery engine may comprise the evaporative surface. In such a configuration, the delivery engine may be placed next to one or more evaporative assistance elements, such as a heater or fan to volatilize the volatile composition into the air. The evaporative assistance elements may surround or at least partially surround the evaporative surface.

Instead of evaporating the volatile composition from an evaporative surface of the delivery engine, the delivery engine may transport the volatile composition to a separate evaporative surface. The evaporative surface may be configured as a porous or semi-porous substrate, a bowl or plate, including a plastic, glass, or metal bowl or plate, and combinations thereof.

The delivery engine may be configured in various ways. For example, the delivery engine may be in the form of a wick, membrane, gel, wax, porous or semi-porous substrate, including a felt pad. In a volatile composition dispenser comprising more than one delivery engine associated with the same or different reservoirs, the delivery engines may be the same or may be different.

If the volatile composition dispenser utilizes a wick as a delivery engine, the wick may be configured to have various different shapes and sizes. For example, the wick may have a cylindrical or an elongate cube shape. The wick may be defined by a length and a diameter or width, depending on the shape. The wick may have various lengths. For example, the length of the wick may be in the range of about 1 millimeter ("mm") to about 100 mm, or from about 5 mm to about 75 mm, or from about 10 mm to about 50 mm. The wick may have various diameters or widths. For example, diameter or width of the wick may be at least 1 mm, or at least 2 mm, or at least 3 mm, or at least 4 mm. A wick may exhibit a density. The wick density may be in the range of about 0.100 grams/cm$^3$ ("g/cc") to about 1.0 g/cc.

A wick may comprise a porous or semi-porous substrate. The wick may be composed of various materials and methods of construction, including, but not limited to, bundled fibers which are compressed and/or formed into various shapes via overwrap (such as a non-woven sheet over-wrap) or made of sintered plastics such as PE, HDPE or other polyolefins. The wick may be made from a plastic material such as polyethylene or a polyethylene blend.

The evaporative assistance element may be used to assist with the evaporation of a volatile composition from the evaporative surface. For example, the evaporative assistance element may be selected from the group consisting of a heater, a fan, an agitation member or agitator that cause vibration, both powered agitator and manual agitator, or combinations thereof. The evaporative assistance element may also include a heating element to heat the liquid volatile composition, a chemical constituent to speed evaporation or evaporation rates, use of a chemically heated membrane to provide increased evaporation via exothermic reaction, or synergistic combinations thereof. The evaporative assistance element may also increase the amount of surface area of a delivery engine exposed to the evaporative assistance element, may cause a pressure gradient, rheostate, etc.

A volatile composition dispenser having an evaporative assistance element in the form of a heater may be configured to heat the evaporative surface to various temperatures. For example, the volatile composition dispenser may be configured such that the heater raises the temperature of the evaporative surface to a temperature of about 30° C. to about 150° C. The heaters can comprise any suitable type of heater, and can be located in any suitable location in or relative to the volatile composition dispenser. The evaporative assistance element may surround or at least partially surround the evaporative surface.

As will be discussed in more detail below, the volatile composition dispenser may include a control system to control the evaporative assistance element.

Figure 2:
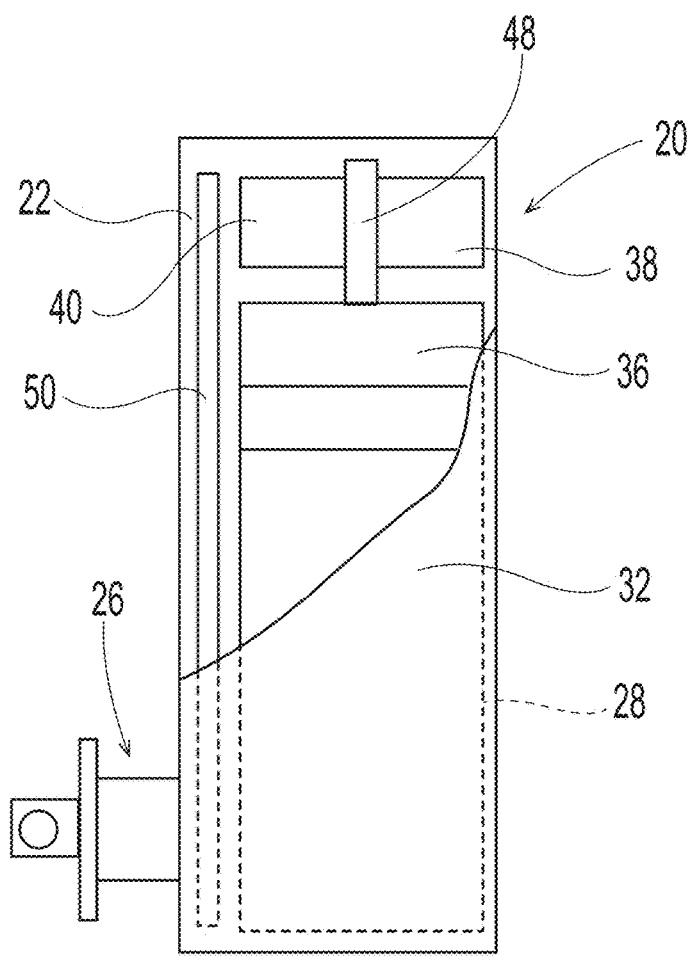
FIG. 2 is a partially fragmented schematic side view of the device shown in FIG. 1.
Figure 3:
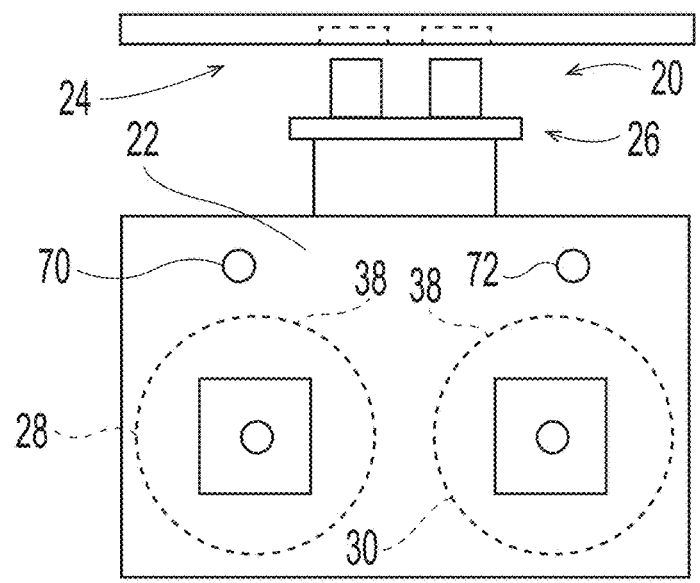
FIG. 3 is a schematic top view of the device shown in FIG. 1.

With reference to FIGS. 1-3, the volatile composition dispenser 20 may take the form of an electrical wall plug volatile composition dispenser. The volatile composition dispenser 20 may include a housing 22, and the housing 22 is supported on an electrical outlet by a power source 26 that is at least indirectly joined to the housing 22. The volatile composition dispenser 20 further comprises at least one reservoir, shown as reservoirs 28 and 30 for illustrative purposes, for containing the volatile compositions, respectively. The housing 22 may serve as a holder for the reservoir(s) 28 and 30 and any of the other components of the volatile composition dispenser 20. The volatile composition dispenser 20 comprises one or more delivery engines 38, shown as wicks in FIGS. 1-3 for illustrative purposes only, extending into each reservoir 28, 30 at one end of the delivery engine and having an evaporative surface 48 at the opposite end. The volatile composition dispenser includes one or more evaporative assistance elements 40, 42, such as a heater as shown in FIGS. 1-3 for illustrative purposes only, for assisting with the evaporation of the volatile compositions from the evaporative surfaces 48. The reservoirs 28 and 30 may contain a first volatile composition 32 and a second volatile composition 34.

Some parts of the volatile composition dispenser may be joined together to form a cartridge 76. For example, the reservoir(s), delivery engine(s), evaporative surface(s), and/or evaporative assistance elements may be joined together as one or more cartridges 76. With reference to FIG. 1, a reservoir 28 or 30, delivery engine 38, and evaporative surface 48 are connected together to form a cartridge 76. The volatile composition dispenser shown vin FIG. 1 includes two cartridges 76, for example.

The cartridges or reservoirs may be replaceable in order to provide a reservoir with a new, different, or replacement volatile composition. Or, the reservoirs may be refillable and reused in the volatile composition dispenser in a new total emission program.

The heaters, such as heaters 40 and 42 shown in FIGS. 1-3 for illustrative purposes only, may comprise heating elements that are in the form of circular rings that at least partially surround the wicks protruding from the bottles of the volatile compositions.

The reservoirs may comprise a seal 36, such as shown in FIG. 1, for containing the volatile composition. The volatile composition dispenser 20 and/or the reservoirs 28 and 30 may further comprise an additional seal for covering the wick 38 when the volatile composition is not being emitted.

While FIG. 1 illustrates two reservoirs, two evaporative assistance elements, and two delivery engines, it is to be appreciated that a volatile composition dispenser may include one, two, three, or more reservoirs. Each reservoir in a volatile composition dispenser may include a separate delivery engine. A single evaporative assistance element may be used for one or more evaporative surfaces or each evaporative surface may be adjacent to a unique evaporative assistance element. If the volatile composition dispenser includes more than one reservoir, each reservoir may contain a different volatile composition or may contain the same volatile composition.

While it is shown in FIGS. 1-3 that the volatile composition dispenser 20 may include two reservoirs, it is to be appreciated that the volatile composition dispenser may comprise one or more than one reservoir. If one reservoir is present, the volatile composition dispenser may include one, two, or more than two delivery engines that are each in fluid communication with the one reservoir and one, two, or more evaporative surfaces that are in fluid communication with the delivery engines. In such a configuration, the volatile composition dispenser may include one or more evaporative assistance elements. If more than one delivery engine is in fluid communication with a single reservoir, than each delivery engine may be used to volatilize the same volatile composition. This configuration may allow for each delivery engine, such as a wick, to have an extended period where the evaporative assistance element is either delivering low energy or is OFF, giving each delivery engine time for the volatile composition to drain and potentially unclog from the delivery engine. Such a configuration may be particularly useful where the delivery engines are in the form of wicks, which can suffer from wick-clogging of components of volatile compositions.

Figure 4:
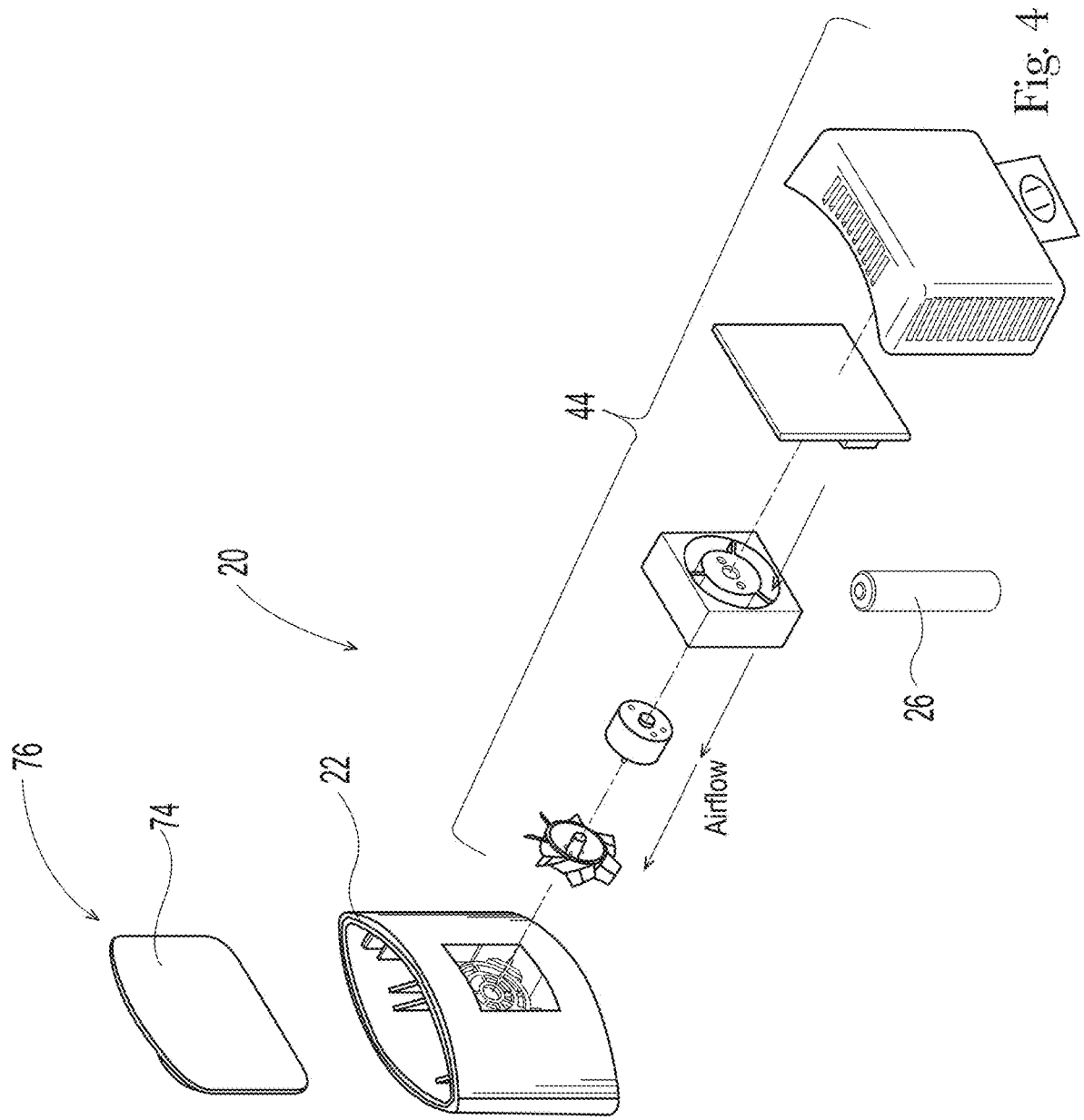
FIG. 4 is a schematic, exploded view of a volatile composition dispenser having a cartridge with a membrane as a delivery engine.
Figure 5:
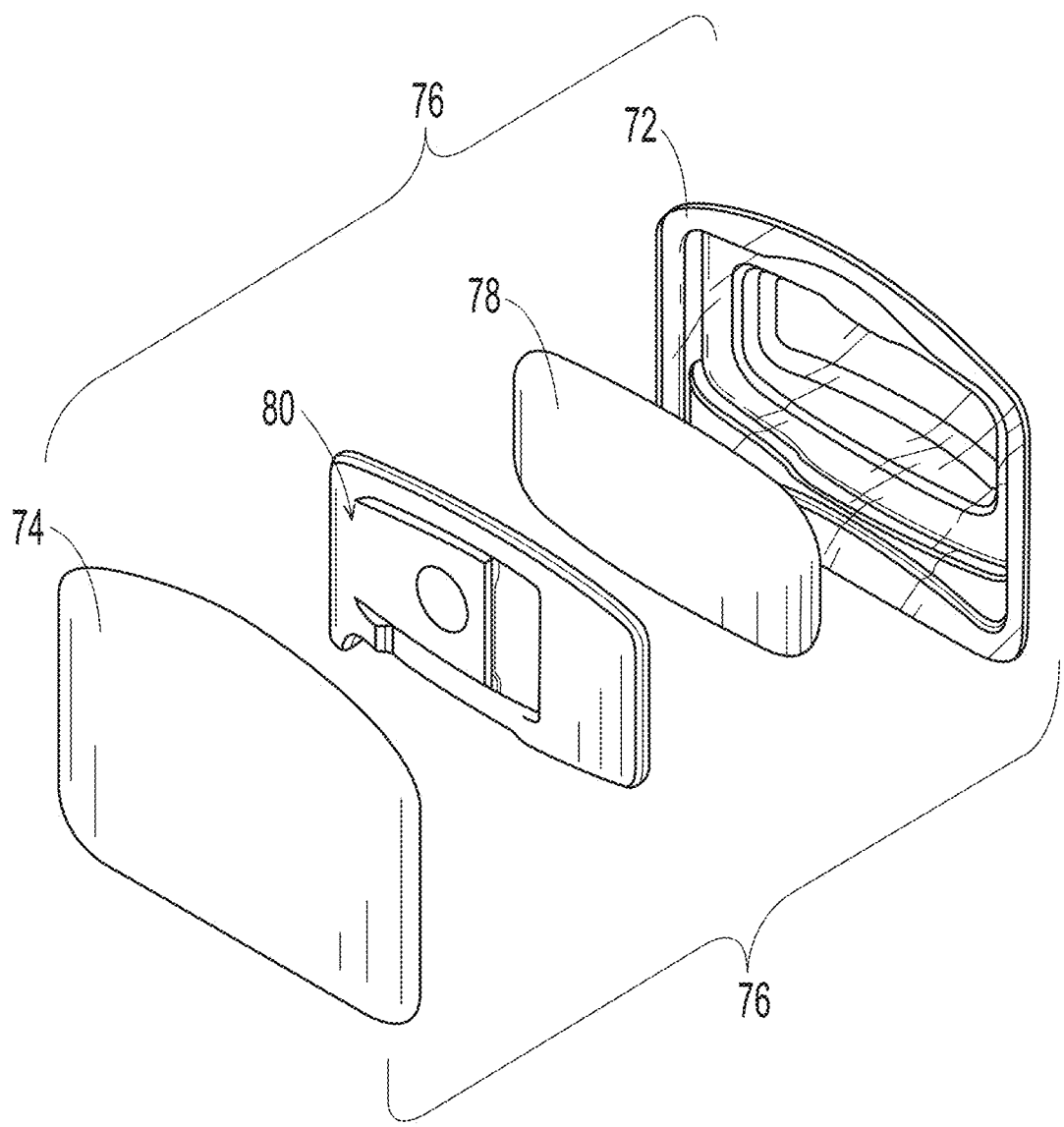
FIG. 5 is a schematic, exploded view of the cartridge of FIG. 4.

Instead of a wick, the delivery engine may be comprised of a breathable membrane. With reference to FIGS. 4 and 5, the volatile composition dispenser 70 may comprise a cartridge 76. The cartridge 76 may include a liquid reservoir 72 for containing a volatile composition and a delivery engine 74 in the form of a breathable membrane enclosing the liquid reservoir 72, such as disclosed in U.S. Pat. Nos. 8,709,337 and 8,931,711. The volatile composition dispenser 70 may also include an evaporative assistance element 44 in the form of a fan as shown in FIG. 5 for exemplary purposes only. As used herein, a breathable membrane is a vapor permeable membrane that prevents free flow of liquid out of the membrane, thus addressing leakage problems.

Suitable breathable membranes include, but are not limited to, UHMWPE-type membrane optionally filled with silica as described in U.S. Pat. No. 7,498,369. Such UHMWPE membranes include Daramic™ V5, available from Daramic, Solupor®, available from DSM (Netherlands), and Teslin™ SP1100HD, available from PPG Industries, and combinations thereof. Other suitable breathable membranes include any permeable polymeric, thermoplastic, or thermoset material, including acetal, acrylic, cellulosic, fluoroplastic, polyamide, polyester, polyvinyl, polyolefin, styrenic, etc, alone, co-extruded, woven or non-woven, mixed or in combination with elastomers, rubber, solids, silicas, or combinations thereof. Also suitable are Hytrel™ available from Dupont or Lotryl™ available from Arkema. The delivery engine 74, such as shown in FIG. 5, may also include a rupturable substrate 78 that seals the volatile composition in the liquid reservoir until a rupture mechanism 80 is engaged to when the volatile composition dispenser is to be used by the consumer. When the consumer is ready to use the volatile composition dispenser, the consumer can rupture the rupturable substrate 78 with the rupture mechanism 80, which allows the volatile composition in the liquid reservoir 72 to contact the breathable membrane.

With reference to FIG. 2, the volatile composition dispenser 20 may include a switching mechanism 50 that changes the volatile composition being emitted by the volatile composition dispenser 20. The switching mechanism 50 can comprise any suitable type of mechanism that causes the volatile composition dispenser to change the volatile composition being emitted. In the embodiment shown, the switching mechanism controls the activation of the evaporative assistance elements, such as heaters, so that the heater will be turned on for the volatile composition that is desired to be emitted. Suitable switching mechanisms include, but are not limited to, analog timing circuitry, digital circuitry, combinations of analog and digital circuitry, microprocessors, and mechanical actuation switches such as shape memory alloys (NiTi wire) or bimetallic switches.

Figure 6:
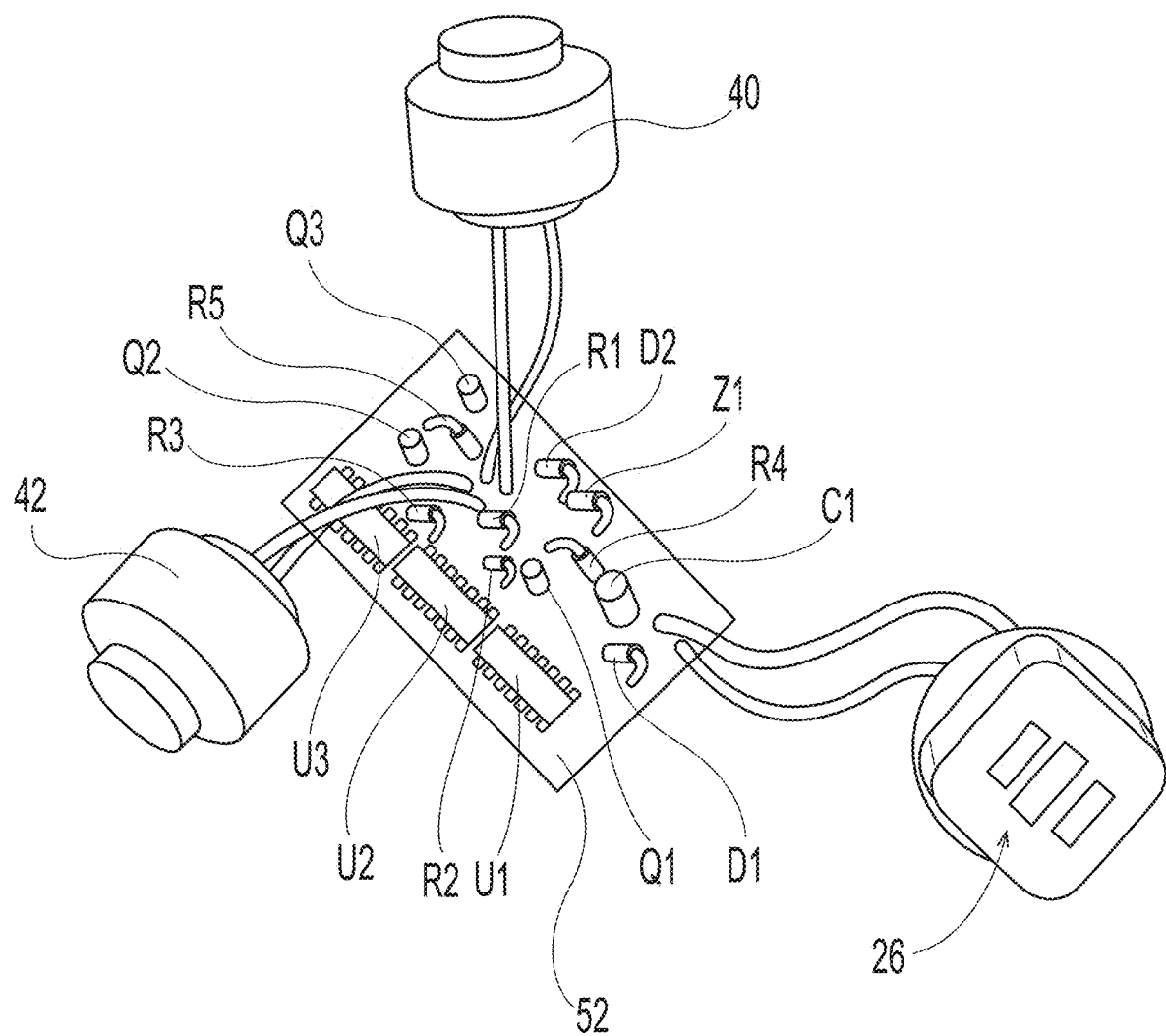
FIG. 6 is a schematic, perspective view of a printed circuit board that can be used to control the volatile composition dispenser shown in FIGS. 1-3, along with heaters and a plug that are attached thereto.

With reference to FIGS. 2 and 6, the switching mechanism 50 may comprise a combination analog and digital circuit in the form of a printed circuit board (or "PCB"). The circuit may include, for in a non-limiting example: a single-sided PC board 52; a capacitor designated C1; a pair of diodes D1 and D2; three transistors Q1, Q2, and Q3; five resistors R1-R5; three counters U1, U2, and U3; a third diode Z1. Where the evaporative assistance elements are heaters, any suitable type of heater can be used, including but not limited to resistance heaters (several types of which are commercially available). The heaters 40 and 42, as well as the power source 26, shown as a wall-mount power plug in FIG. 6, are also connected to the circuit board 52 by wires 66. Suitable components for circuit are set out in the following table:

TABLE 1

| Reference Number or Letter | Component | Properties |
| --- | --- | --- |
| C1 | Capacitor, Electrolytic | 1 microF, 250 V |
| D1, D2 | Diode | 1N4004, or similar |
| 26 | Wall power plug | |
| Q1, Q2, Q3 | Transistors, NPN | NPN 200 V, 200 mA |
| R1-R5 | Resistors | 1/8 watt |
| U1, U2, U3 | Counters | CD4024, or similar |
| Z1 | Diode, Zener, 11 V | 1N4741A, or similar |

Figure 7:
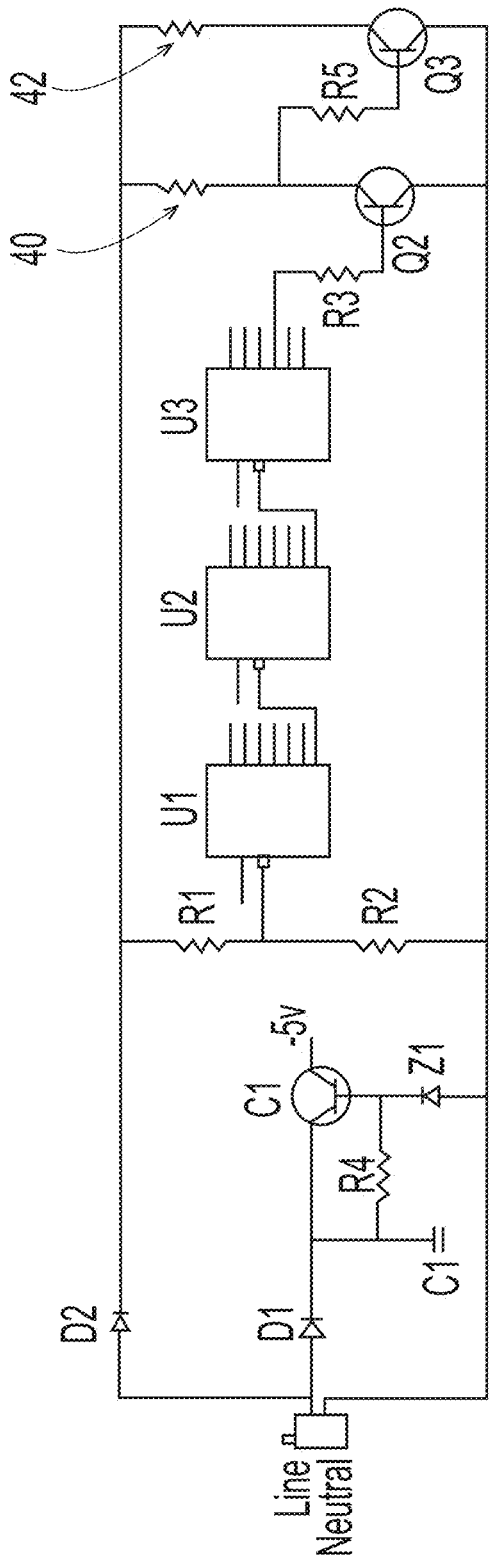
FIG. 7 is a schematic of the circuit shown in FIG. 6.

The components of the circuit may be through-hole or surface mounted. In the configuration shown in FIG. 6, a 38×66 mm single sided PC board 52 with through-hole components is used. The material comprising the PC board 52 can be a standard material such as FR-4 epoxy base fiberglass, but any UL approved material is acceptable. The power source 26 shown in FIG. 6 is a molded wall plug with approximately 100 mm pigtails into the PC board. FIG. 7 is a schematic for one example of a circuit. This circuit provides a timing function that alternates current between two paths over a time period of several tens of hours, with a pre-selected time for each heater to be turned ON and OFF.

The switching mechanism may include, but is not limited to, the following alternative types of switching mechanisms: (1) a magnetic sensor with a pickup that counts the number of rotations of the motor of a fan used to disperse the volatile composition(s) such that after a certain number of rotations, the volatile composition dispenser will switch from one volatile composition to another; and (2) a volatile composition dispenser comprising dual shape memory alloys, or bimetallic strips or switches that can complete a circuit at ambient temperature and then cut-off when a certain temperature is reached. The two-way effect can be used since as the temperature lowers, the material can complete the circuit again, thus acting as a thermostat to keep the heater on and then turn it off. The shape memory alloy may serve as the heater as well as the pulse generator.

Figure 8:
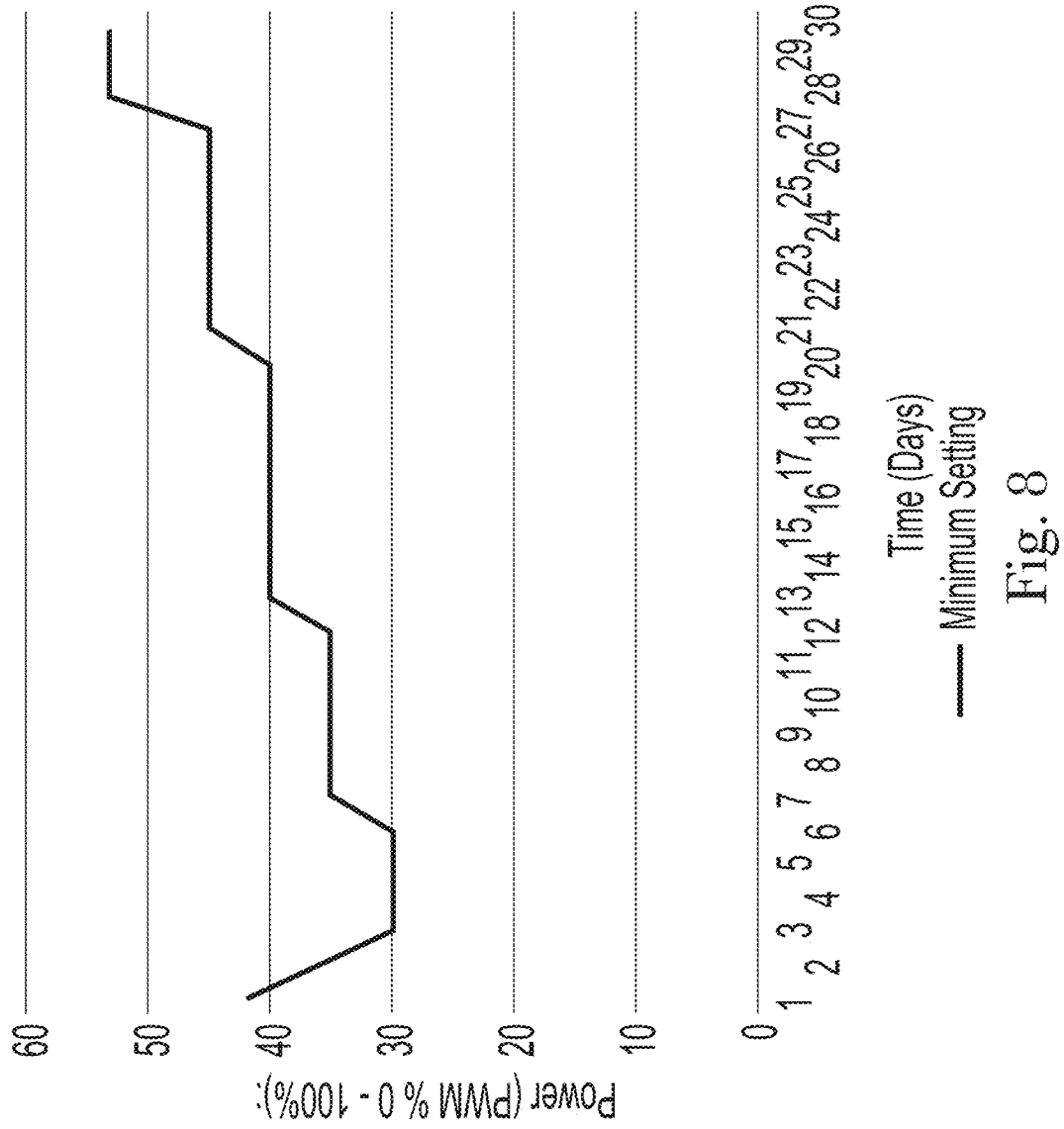
FIG. 8 is plot of a total emission program for a volatile composition dispenser, expressed as a percentage of maximum heater power over time.

The volatile composition dispenser 20 can comprise a number of additional optional features. The volatile composition dispenser can be provided with indicators so that a person is further made aware that the volatile material being emitted has changed. Such indicators can be visual and/or audible, such as lights or sounds, respectively. For example, in the case of scented materials, such an indicator may allow a person to see which scent is being emitted at a given time. With reference to FIGS. 6-8, the indicators may be in the form of lights 70 and 72. In another example, at least a portion of the volatile composition dispenser 20 (such as all or a portion of the housing) or the reservoirs may be made of a type of plastic that changes color when heated.

The volatile composition dispenser can be provided with additional user controls. The volatile composition dispenser can include a power switch to allow a user to turn the volatile composition dispenser ON and OFF without removing it from the electrical socket. The volatile composition dispenser can be provided with a control that allows the user to control the discrete emission period of one or more of the volatile compositions, and/or the time between the emission of the different volatile compositions, or the time that the volatile materials are emitted during a simultaneous operation period. For example, in one non-limiting example, if the volatile composition dispenser is provided with the capability of emitting each volatile material during a period greater than 15 minutes and less than or equal to 48 hours, then the volatile composition dispenser can be provided with a control that allows the user to set the discrete emission period for one or more of the volatile compositions to 30 minutes, 45 minutes, or 72 minutes, or to one hour, for example.

The volatile composition dispenser can be provided with additional user controls. The volatile composition dispenser can comprise a thermostat or other switch to allow a user to adjust the temperature settings of the heat sources for one or more of the volatile compositions. The settings may be predefined for particular volatile compositions, or may be adjustable based on selected temperatures to be applied to a wick. The settings may include a LOW and HIGH settings or LOW, MEDIUM, and HIGH settings, for example, that a user can set either directly on the volatile composition dispenser or remotely through a remote control (computer, phone, etc). A device may have one, two, three, four, five, six, or more different intensity settings. The settings may be labeled as an intensity (i.e. HIGH, MEDIUM, LOW, etc.) or room-type (i.e. bathroom, bedroom, living, kitchen, etc.).

The volatile composition dispenser may also include sensors and the volatile composition dispenser may be programmed to adjust for the readings of the sensors. For example, the volatile composition dispenser may include sensors such as temperature sensors, relative humidity sensors, volatile material sensors, light sensors (e.g., detecting day/night), and the like.

The volatile composition dispenser may be communicably connectable with various components of the dispenser, including the sensor(s), evaporative assistance elements, user interface, etc., using a wireless communication link. Various wireless communication links may be used, including 802.11 (Wi-Fi), 802.15.4 (ZigBee, 6LoWPAN, Thread, JennetIP), Bluetooth, combinations thereof, and the like. Connection may be through an ad hoc Mesh Network protocol. The controller may include a wireless communication module in order to establish a wireless communication link with the controller with various components of the system. Any module known in the art for establishing such communication links can be utilized. The controller may include utilize a machine learning algorithm, such as a NEST® learning thermostat.

The cartridge or reservoir may include an identification tag, such as an RFID tag and the housing of the volatile composition dispenser may include an RFID tag reader. An RFID tag may be used to tell the controller details about the volatile composition contained in the cartridge or reservoir, such as the scent. The volatile composition dispenser may include programs that adjust to account for information read from the RFID tag.

The volatile composition dispenser may include a tactile switch or registration point that, upon coming in contact with a cartridge or reservoir, provides signals to the volatile composition dispenser including, but not limited to, a new or refilled cartridge or reservoir that is full of a volatile composition has been inserted, an old cartridge or reservoir has been removed, etc. The PCB would interpret these signals and cause the volatile composition dispenser to act to programmed instructions accordingly, such as starting the total emission program for a new or refilled cartridge that is "full" of a volatile composition.

The volatile composition dispenser can also be sold in the form of a kit that includes the volatile composition dispenser and one or more reservoirs of volatile compositions. The volatile composition dispenser and/or kit can also include instructions for use that instruct the user regarding certain discrete emission periods that may be used to produce certain results, and/or instructions regarding where to place the volatile composition dispenser in a given space. For example, the instructions may include instructions for setting the volatile composition dispenser based on the size of the room, vehicle, etc. in which the volatile composition dispenser is placed. Such instructions may also include instructions to the user to choose more frequent changes between the emissions of scented materials for greater scent awareness. Instructions may also be provided to specify how to operate the volatile composition dispenser relative to other volatile composition dispensers. The instructions can be provided in any suitable form, e.g., written, audio, and/or video.

The volatile composition dispenser may include a power source, such as a plug or battery. The volatile composition dispenser may be battery powered so that it need not be plugged into an electrical outlet. If a plug is used as the power source to connect to an electrical outlet, the plug may include a cord or may be a wall-mount plug. The volatile composition dispenser can also be configured so that it can be both plugged in and powered by a source of electrical current, and also battery powered. The volatile composition dispenser can also be provided with an adapter so that it can be plugged into the cigarette lighter in a vehicle. In addition, the volatile composition dispenser can be provided with a remote control that allows the user to control any, or all, of the emission properties of the volatile composition dispenser (including, but not limited to changing the volatile material being emitted) without touching the volatile composition dispenser.

The volatile composition dispenser may comprise a microprocessor that has less component parts compared to analog circuits, and improved circuit quality from lot to lot. The microprocessor can allow the user to program and control the temperature profile by modulation to alter performance. If desired, the microprocessor may be connected to a user interface. This can be any suitable type of user interface. Examples of types of user interfaces include, but are not limited to LCD screens and LEDs, buttons (push buttons or buttons that move side-to-side), dials, and the like. In addition, the microprocessor enables components to allow multiple volatile composition dispensers (such as those located in different parts of a room, or in different rooms), to communicate with each other. For example, the microprocessor can enable a remote control to send digital signals via an infrared beam to turn another volatile composition dispenser ON or OFF.

The evaporative assistance elements, such as a heater or fan, may be programmed to operate in various operational conditions. As will be discussed in more detail below, the evaporative assistance elements may be configured to have various discrete emission periods, gaps in emission of any evaporative assistance elements, varying energy profiles over time, randomized energy profiles, simultaneous emission periods, and combinations thereof. Each of these methods of operation, either alone or in combination, may promote user noticeability of the volatile composition and/or reduce the likelihood of short-term or long-term habituation of the volatile composition.

The term "discrete emission period", as used herein, refers to the individual time period that a given volatile composition is emitted in an emission sequence. This may correspond generally to the period of time that an evaporative assistance element is turned ON for a given fill of volatile composition, although there may be a slight lag between the operation of an evaporative assistance element and the emission of a volatile composition. The term "extended emission periods", as used herein, includes a plurality of successive discrete emission periods that may be separated by gaps in operation where the evaporative assistance element is OFF.

The "total emission program" refers to the entire sequence, including all discrete emission periods and OFF times for gaps in emission that make up the energy boosts and extended emission periods, from beginning to end of life of a "filled" volume of volatile composition in a cartridge. "Fill" or "filled" as used herein refers to an amount of volatile composition that is intended to occupy the whole of or substantially the whole of the available volume in the reservoir, which excludes any volume occupied by any other elements of the volatile composition dispenser that may be disposed in the reservoir, such as the delivery engine. The reservoir will typically be occupied or filled to least 80%, 85%, 90%, or 95% volatile composition, of the total available volume of the reservoir. The total emission program is then designed to evaporate all or substantially all of the volatile composition in the reservoir.

The total emission program may be continuous. The term "continuous", as used in reference to the emission program, means that there is a planned emission sequence over an entire period, once the program is initiated. This emission program can include periods, as noted above, where there are gaps in emission. This will still be considered to be a continuous emission program, although there will not necessarily be continuous emission of volatile compositions. It should be understood, however, that it is possible for the emission program to be interruptible by the user (e.g., turned off), if desired. Thus, the method can provide a user interface, and the user interface can provide a user with the ability to interrupt emission program. The emission program may be designed to run continuously, or substantially continuously until at least one of the volatile compositions is substantially depleted from the cartridge. It may be desirable for the emission program to run continuously until all of the volatile compositions are substantially depleted, and for this to occur at approximately the same time.

If the total emission program is disrupted, the dispenser may be configured with memory to record the last emission sequence that was initiated in the event that the volatile composition dispenser is disconnected from the power source. Once operation of the volatile composition dispenser is resumed, the memory of the last recorded sequence is recalled to return the total emission program to the correct emission sequence. The total emission program may only be restarted at the beginning of the program when a new or refilled reservoir/cartridge is installed into the housing.

The total emission program can be of any suitable length, including but not limited to 10 days, preferably 15 days, preferably 20 days, preferably 25 days, preferably 30 days, more preferably 45 days, more preferably 60 days, more preferably 90 days, more preferably 130 days, more preferably 150 days, or shorter or longer periods, or any period between 30 to 150 days.

The discrete emission period for each evaporative assistance element in a volatile composition dispenser may be in the range of 2 minutes to 48 hours, alternatively 5 minutes to 48 hours, alternatively 10 minutes to 48 hours, alternatively 15 minutes to 48 hours, alternatively 20 minutes to 24 hours, alternatively 30 minutes to 8 hours, alternatively 45 minutes to 4 hours. The higher the energy supplied by the evaporative assistance element, such as a higher temperature supplied by a heater, the shorter the discrete emission period that may be needed to provide a noticeable amount of volatile composition into the air.

During the discrete emission period for a particular evaporative assistance element, the evaporative assistance element will be continuously ON. In a volatile composition dispenser comprising more than one evaporative assistance element, the evaporative assistance elements may have alternating discrete emission periods. In an alternating system, one evaporative assistance element may be turned ON while the other evaporative assistance element(s) may be turned OFF. Or, one or more evaporative assistance elements may be turned ON at a given time. The operation of two or more evaporative assistance elements may overlap for a period of time. The greater the discrete emission period for each evaporative assistance element, the potential for higher concentrations of volatile composition in the surrounding space in order to increase user noticeability. There may also be time periods when all evaporative assistance elements are turned OFF. Each evaporative assistance element may be configured to have the same discrete emission period, or some or all of the evaporative assistance elements may be configured to have different discrete emission periods.

Evaporation rates of the volatile composition from the evaporative surface may be between 5 mg/hr and 200 mg/hr, preferably between 10 mg/hr and 100 mg/hr, more preferably between 10 mg/hr and 80 mg/hr, more preferably between 15 mg/hr and 60 mg/hr, and more preferably between 15 mg/hr and 50 mg/hr, and more preferably 15 mg/hr to 35 mg/hr over the total emission program.

Near the end of the total emission program, the volatile composition dispenser may operate at or near the maximum power output, such as maximum temperature or fan speed, until unplugged and a new cartridge or reservoir is installed.

The total emission program may be configured to turn OFF an evaporative assistance element when the volatile composition is depleted from the reservoir. For example, the evaporative assistance element may turn OFF after a predetermined time period for a given intensity setting. By turning OFF the evaporative assistance element, energy is not applied by the evaporative assistance element until the reservoir is refilled or replaced with a new fill of volatile composition.

Varying Energy

Varying the energy applied by the evaporative surface over the total emission program may improve consumer noticeability of the volatile composition and help prevent habituation of the volatile composition. In order to increase noticeability of the volatile composition evaporated from the volatile composition dispenser and prevent noticeability from continually declining over the life of the volatile composition in the volatile composition dispenser, the evaporation rates may be constant, substantially constant, increasing, or variable. In order to achieve constant, substantially constant, increasing, or variable evaporation rates, the energy applied to the evaporative surface by the evaporative assistance element can be varied to achieve the desired evaporation profile over the total emission program. For example, in order to deliver a constant, substantially constant, or even increasing evaporation rate over time, the power of the evaporative assistance element and/or the ON-time of the evaporation assistance element can be continually increased over time. In order to achieve an increasing evaporation rate over time, the power applied by the evaporative assistance element and/or the ON-time of the evaporative assistance element may need to be greater than the power applied and/or the ON-time of the evaporative assistance element as compared to the operation of an evaporative assistance element programmed to maintained a constant or substantially constant evaporation rate. In order to create a random or variable evaporation rate over the total emission cycle, the power applied by the evaporative assistance element and/or the ON-time of the evaporative assistance element can be increased, maintained, and/or decreased over time. The energy applied to the evaporative surface may be adjusted at a variety of frequencies.

The energy applied by the evaporative surface through the evaporative assistance element may be in the form of heat, an exothermic reaction, air flow, and the like. Operating the evaporative assistance element for an extended length of time can have the same, similar, or additive effect on the evaporation of the volatile composition as increasing the power to the evaporative assistance element over a comparatively shorter time period. Another method of increasing the energy applied to the evaporative surface, either alone or in combination with the selection of evaporative assistance element, may include adjusting the amount of surface area of the evaporative surface exposed to the evaporative assistance element. For example, an energy boost could include exposing more of the evaporative surface to the evaporative assistance element; similarly, a decrease in energy could also be attributed to a decrease in exposed surface area of the evaporative surface.

The energy applied to the evaporative surface can either be increased; decreased, or maintained at any given point within the total emission program. It has been found that a total emission program having a combination of extended emission periods of increased energy ("energy boost"), decreased energy, and/or maintained energy provides improved consumer acceptance of a volatile composition dispenser over commercially available volatile composition dispensers.

It has been found that consumers expect a minimum level of noticeability of the volatile composition at the beginning of life of a cartridge. A volatile composition dispenser that meets this expectation at the beginning of life can actually improve consumer acceptance of the volatile composition dispenser not only at the beginning of life, but for the total emission program. As such, an energy boost period of a relatively high energy at the beginning of the total emission program to meet or exceed the consumer's minimum level of noticeability requirement may be desirable. Thus, an initial energy boost period applied to the evaporative surface within the first 24 hours of operation of the total emission program of the volatile composition dispenser should be sufficiently high to meet or exceed the consumer's minimum desired evaporation rate for the volatile composition.

An energy boost at various extended emission periods over the life of the volatile composition in the reservoir can increase noticeability of the volatile composition over the total emission program by maintaining or increasing the evaporation rate of the volatile composition from the evaporative surface over time.

The total emission program may also include extended emission periods of decreased energy applied to the evaporative surface. Decreasing the energy applied to the evaporative surface for periods of time can conserve the volatile composition such that the volatile composition may extend the total time of the total emission program. Decreasing the energy applied to the evaporative surface can also improve noticeability over time because a subsequent energy boost may result in a bigger change in energy over the same time period.

The total emission program may also include extended emission periods of maintained energy applied to the evaporative surface. Maintaining the energy applied to the evaporative surface in between periods of an energy boost can conserve the volatile composition such that the volatile composition may deplete from the cartridge slower. Applying an energy boost more frequently than is needed to increase consumer noticeability may be volatilizing more volatile composition than is necessary.

The extended emission periods may include periods of decreasing energy, maintained energy, relatively small increases in energy that remain below the energy of the previous or subsequent energy boost, or combinations thereof.

The length of an energy boost period may extend for up to half of the length of the extended emission periods of decreasing and/or maintaining energy. Or, length of an energy boost may extend for up to one-third of the length of the extended emission periods of decreasing and/or maintaining energy. An energy boost may occur on a daily, weekly, or biweekly basis with extended emission periods in between.

In a configuration where the evaporative assistance element(s) is a heater, the energy boosts may include an increase in temperature. In such a configuration, one energy boost may be at a temperature in the range of about 40° C. to about 80° C., wherein a subsequent energy boost may be at a temperature in the range of about 50° C. to about 90° C., and a subsequent energy boost may be at a temperature in the range of about 60° C. to about 100° C.

In a configuration wherein the energy is adjusted through the length of time of the discrete emission periods for the evaporative assistance element(s), one energy boost may have a discrete emission period(s) of 20 minutes to 90 minutes, a subsequent energy boost may have a discrete emission period(s) of 40 minutes to 110 minutes, and a subsequent energy boost may have a discrete emission period(s) of 60 minutes to 130 minutes.

An energy boost period may increase the energy by at least 5%, or at least 10%, or at least 15%, or at least 20%, or at least 30%, or at least 40%, or at least 50%, or at least 60%, or at least 75%, or at least 100%, or at least 150%, or at least 200% of the energy applied immediately before the energy boost period. The greater the increase in energy at an energy boost period, the more noticeable the volatile composition may be to the consumer during and following the energy boost period. Successive energy boost periods in a total emission program may increase by a greater percentage than the previous energy boost periods in order to achieve the desired uniform or increased evaporation rate.

An energy boost period may increase the evaporation rate by at least 5%, or at least 10%, or at least 15%, or at least 20%, or at least 30%, or at least 40%, or at least 50%, or at least 60%, or at least 75%, or at least 100%, or at least 150%, or at least 200% of the evaporation rate before the energy boost period.

Energy boost period may occur over a length of time that is shorter than the length of time of an extended emission period in order to extend the life of the volatile composition in the reservoir. As such, the length of time of an energy boost period may be no more than half of the length of an extended emission period, or the length of an energy boost period may be no more than one third of the length of an extended emission period. An energy boost period may occur over the course of 1 day and an extended emission period may occur over the course of 2 to 6 days, for example. Or an energy boost may occur over the course of 2 days and an extended emission period may occur over the course of 4 to 6 days, for example.

Throughout the detailed description and claims, the energy boosts may be referred to as "a first energy boost", a "second energy boost", "a third energy boost" etc. It is to be understood that the number used with the term "energy boost" is used only to different between different energy boosts and is not intended to limit the order in which the energy boosts occur. That is, an additional energy boost or multiple energy boosts may occur between two sequentially numbered energy boosts. For example, "second energy boost" and a "third energy boost" may be separated by an additional one or more energy boosts.

A total emission program may follow a planned emission sequence such as Program 1 having the energy boost periods and extended emission periods described below and illustrated in FIG. 8.

PROGRAM 1

1. a first energy boost at a first energy;
2. a first extended emission period of decreasing or constant energy that remains below the first energy;
3. a second energy boost at a second energy;
4. a second extended emission period operated at the second energy;
5. a third energy boost;
6. a third extended emission period operated at the third energy;
7. a fourth energy boost;
8. a fourth extended emission period operated at the fourth energy;
9. a fifth energy boost; and
10. a fifth extended emission period operated at the fifth energy.

The energy in Program 1 was is varied by adjusting the percentage of maximum power output that the evaporative assistance element is operating at in a given period. Altering the % of maximum power output can be used alone or in combination with adjusting discrete emission periods in a system having more than one evaporative assistance element.

Figure 9:
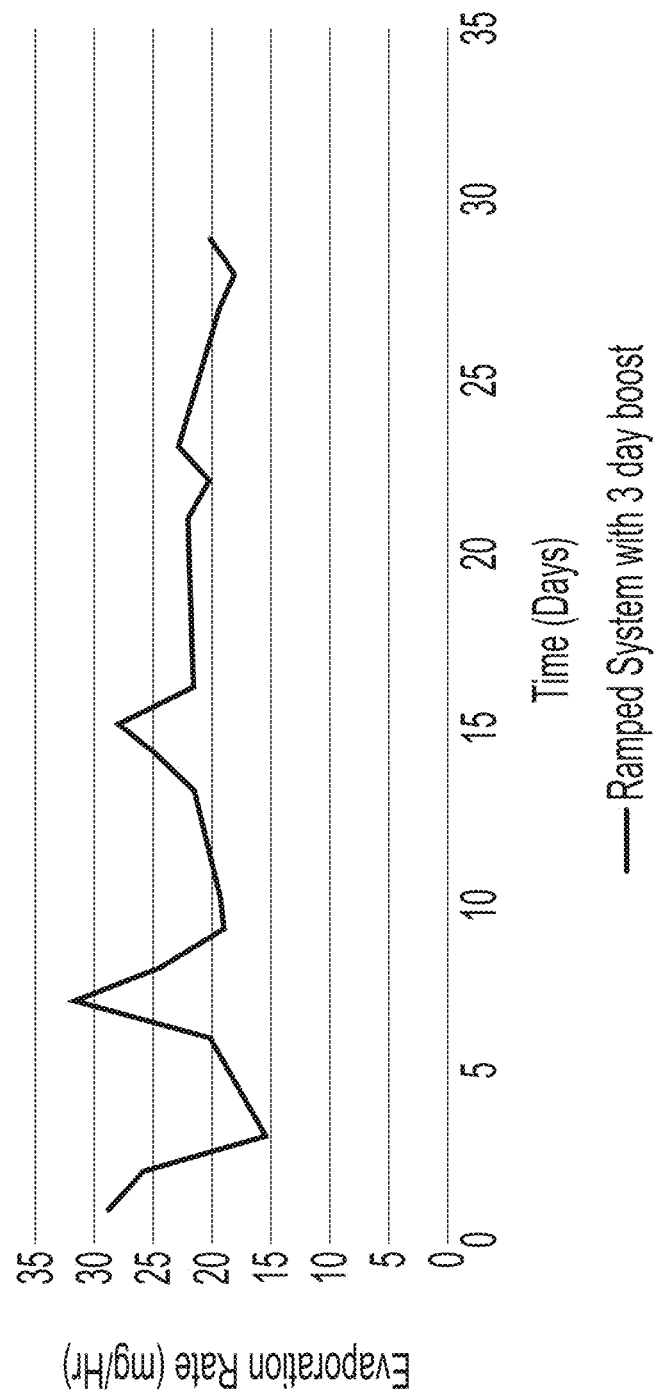
FIG. 9 is a plot of the evaporation rate of the volatile composition dispenser operating with the total emission program of FIG. 8.
Figure 10:
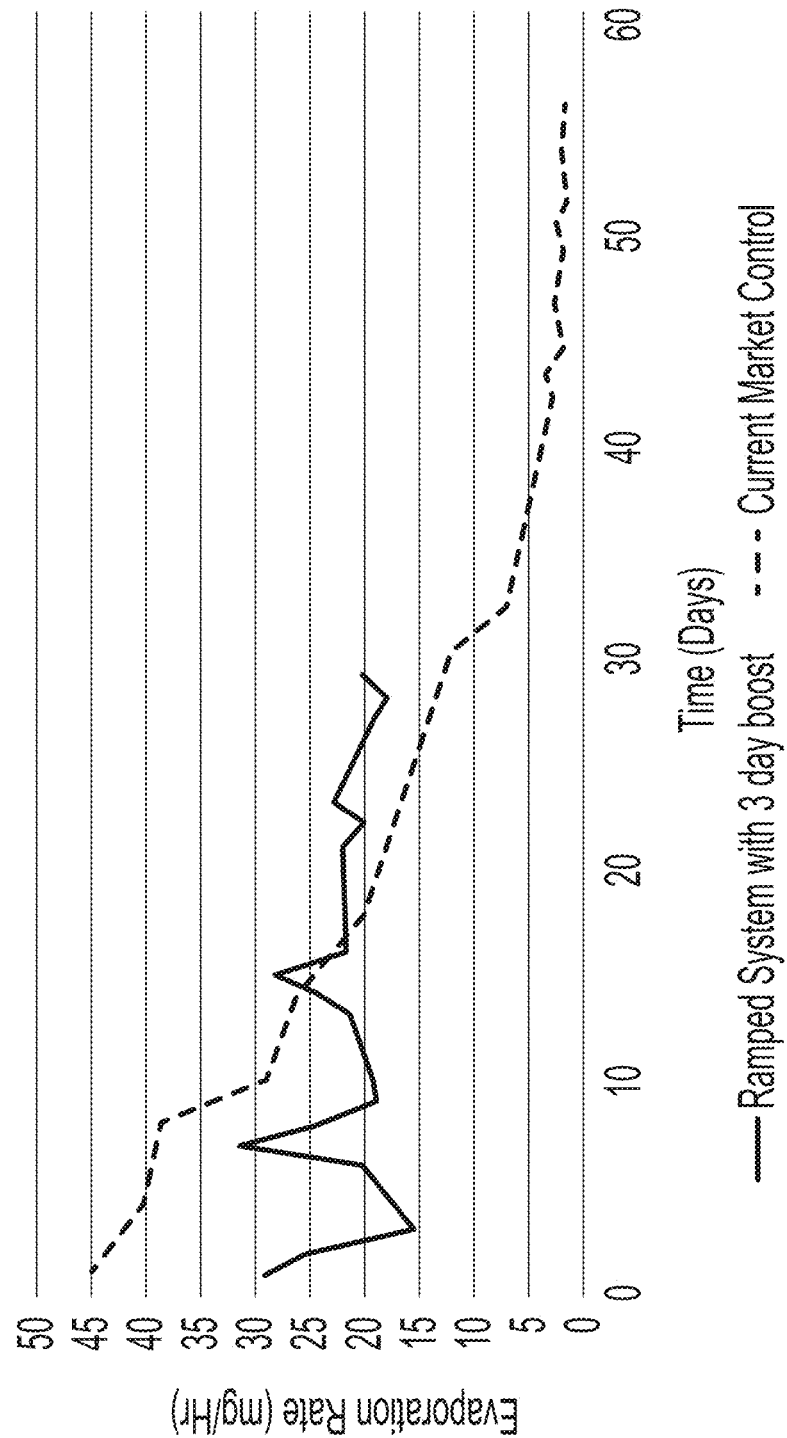
FIG. 10 is a plot of the evaporation rate of the volatile composition dispenser of FIG. 9 overlaid with a plot of the evaporation rate of a current market device.

Program 1 results in evaporation rates shown in FIG. 9. Generally, the evaporation rate of the volatile composition starts at an initial evaporation rate, gradually declines, increases with each applied energy boost, and then follows a generally constant or very slowly decreasing evaporation rate. The energy boosts provide an increase in consumer noticeability throughout the total emission program. The energy boosts over the total emission program followed by extended emission periods of maintained energy result in operation within a narrow, consumer preferred evaporation rate range over time, compared with a current-market control device that gradually declines in evaporation rate over time, such as shown in FIG. 10.

Program 1 may be modified to include additional extended emission periods or to include fewer extended emission periods. Program 1 could include additional or fewer energy boost periods.

Each extended emission period of the total emission program may last for different lengths of time. For example, an energy boost may be applied for a period of one day or two days. Discrete emissions steps of decreasing energy and/or periods of maintained energy may last for a period of at least one day, or at least two days, or at least three days, or at least four days, or at least five days, or at least six days.

Figure 11:
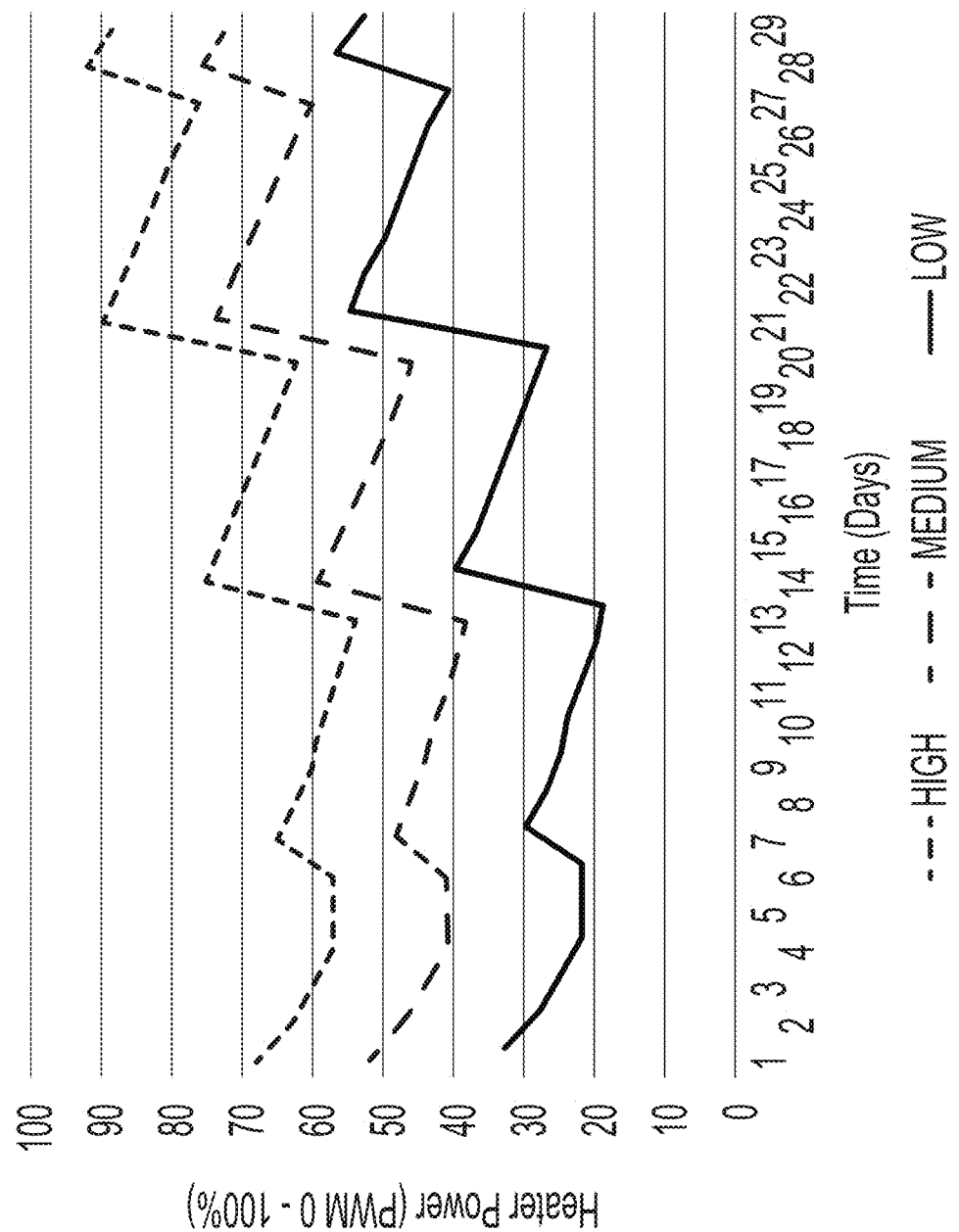
FIG. 11 is a plot of the total emission program for a volatile composition dispenser having HIGH, MEDIUM, and LOW power settings, expressed as a percentage of maximum heater power over time.

A total emission program may follow a planned emission sequence such as Program 2 having the energy boosts and extended emission periods described below and illustrated in FIG. 11.

11. a first energy boost at a first energy;
12. a first extended emission period of decreasing or constant energy that remains below the first energy;
13. a second energy boost at a second energy;
14. a second extended emission period operated below the second energy;
15. a third energy boost;
16. a third extended emission period operated below the third energy;
17. a fourth energy boost;
18. a fourth extended emission period operated below the fourth energy;
19. a fifth energy boost; and
20. a fifth extended emission period operated below the fifth energy.

The energy in Program 2 was is varied by adjusting the percentage of maximum power output that the evaporative assistance element is operating at in a given period. Altering the % of maximum power output can be used alone or in combination with adjusting discrete emission periods in a system having more than one evaporative assistance element.

Figure 12:
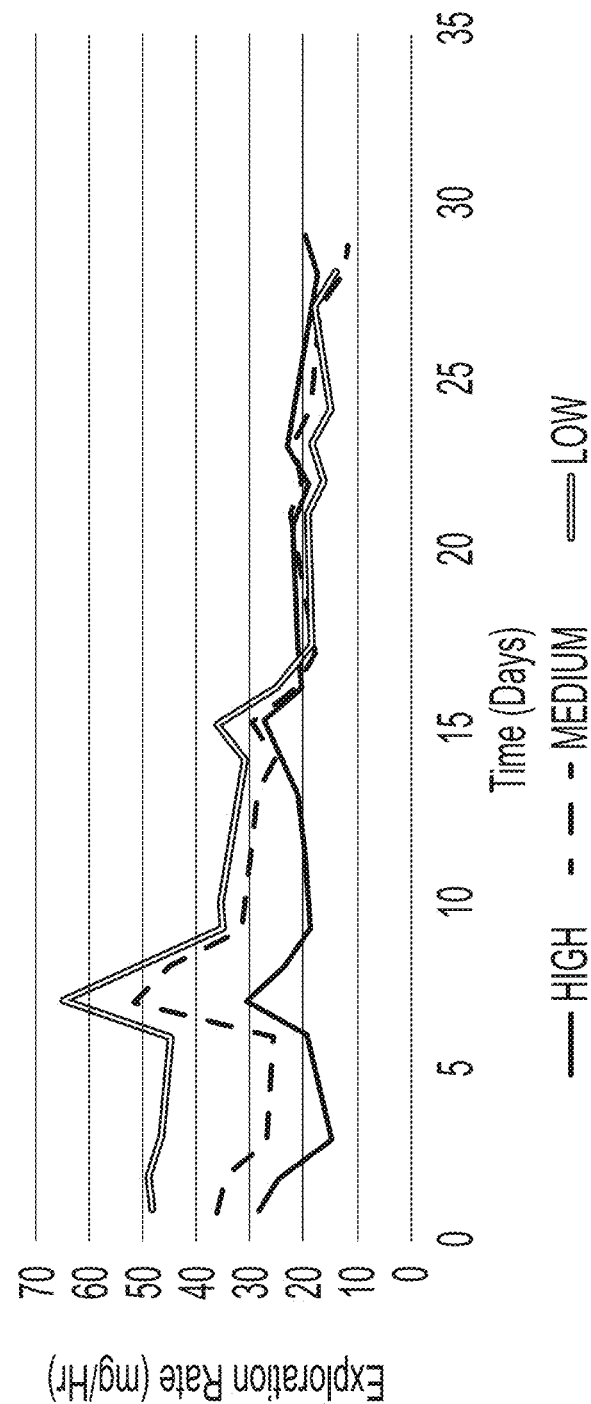
FIG. 12 is a plot of the evaporation rates for HIGH, MEDIUM, and LOW settings for the total emission program of FIG. 11.

A volatile composition dispenser may be configured to have multiple user-controlled settings, such as HIGH, MEDIUM, and LOW or HIGH and LOW, for example. FIG. 12 illustrates the total emission program for Program 2 for a volatile composition dispenser that has HIGH, MEDIUM, and LOW settings. For HIGH, MEDIUM, and LOW settings, the energy applied to the evaporative surface follows the same general extended emission periods of Program 2 over the total emission program, just at different energy levels, with HIGH using the highest energy levels and LOW using the lowest energy levels.

Program 2 may be modified to include additional energy boosts or additional extended emission periods of decreasing energy or maintained energy. Program 2 may also be modified to include fewer extended emission periods than shown. Each extended emission period of the total emission program may last for different lengths of time. For example, an energy boost may be applied for a period of one day or two days. Extended emission periods of decreasing energy and/or periods of maintained energy may last for a period of at least one day, or at least two days, or at least three days, or at least four days, or at least five days, or at least six days.

A total emission program may follow a planned emission sequence such as Program 3 described below and illustrated in FIG. 13.

1. a first energy boost at a first energy;
2. a first extended emission period of decreasing or constant energy that remains below the first energy;
3. a second energy boost a second energy;
4. a second extended emission period operated below the second energy;
5. a third energy boost a third energy;
6. a third extended emission period operated below the third energy;
7. a fourth energy boost a fourth energy;
8. a fourth extended emission period operated below the fourth energy;
9. a fifth energy boost a fifth energy;

10. a fifth extended emission period operated below the fifth energy;
11. a sixth energy boost a sixth energy;
12. a sixth extended emission period operated below the sixth energy;
13. a seventh energy boost a seventh energy;
14. a seventh extended emission period operated below the seventh energy.

The energy in Program 3 was is varied by adjusting the length of the discrete emission periods of the evaporative assistance element. Altering the length of the discrete emission periods can be used alone or in combination with altering the percentage of maximum power output of the evaporative assistance element.

Figure 13:
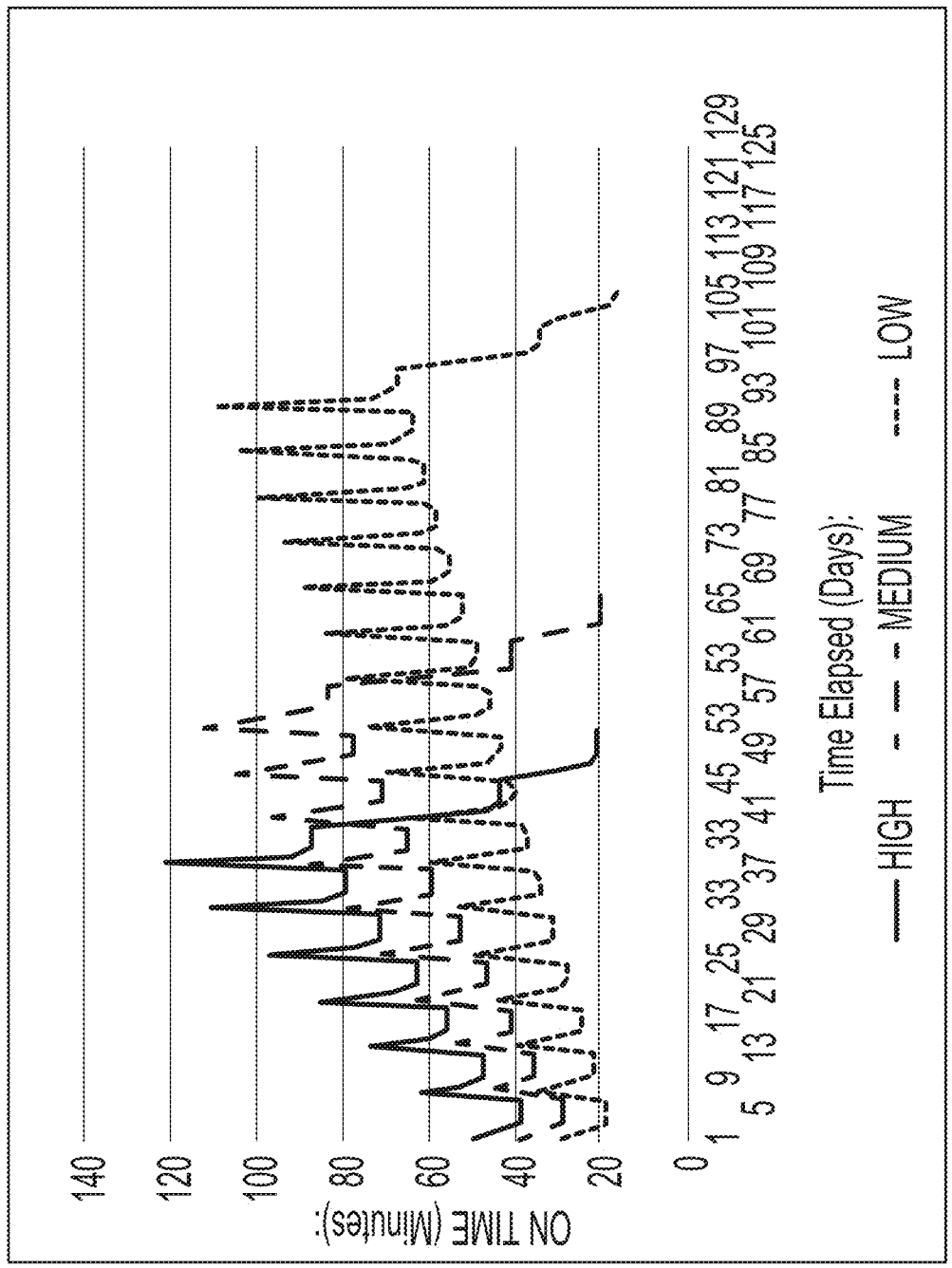
FIG. 13 is a plot of the total emission program for a volatile composition dispenser having HIGH, MEDIUM, and LOW power settings, expressed as the length of ON-time of the heaters.

The total emission program for Program 3 for a volatile composition dispenser has HIGH, MEDIUM, and LOW settings shown in FIG. 13. For HIGH, MEDIUM, and LOW settings, the energy applied to the evaporative surface follows the same general extended emission periods of Program 3 over the total emission program, just at different lengths of discrete emission periods for the evaporative assistance element, with HIGH having the longest discrete emission periods and LOW having the shortest discrete emission periods.

Program 3 may be modified to include additional energy boosts or additional extended emission periods of decreasing energy or maintained energy. Program 3 may also be modified to include fewer extended emission periods than shown. Each extended emission period of the total emission program may last for different lengths of time. For example, an energy boost may be applied for a period of 1 day or 2 days. Extended emission periods of decreasing energy and/or periods of maintained energy may last for a period of at least 1 day, or at least 2 days, or at least 3 days, or at least 4 days, or at least 5 days, or at least 6 days.

Program 1, 2, and 3, or any modification thereof, may be used for a volatile composition dispenser having one or more evaporative assistance elements, evaporative surfaces, and/or cartridges. Each evaporative assistance element may follow Program 1, 2, 3, or any modification thereof, or one evaporative assistance may follow Program 1, 2, 3, or any modification thereof, and any additional evaporative assistance element may follow a different total emission program along with the evaporative assistance element operating under Program 1, 2, 3 or any modification thereof. The evaporative assistance elements may alternate operation of the same or of different total emission programs.

Uniform Evaporation

Figure 14:
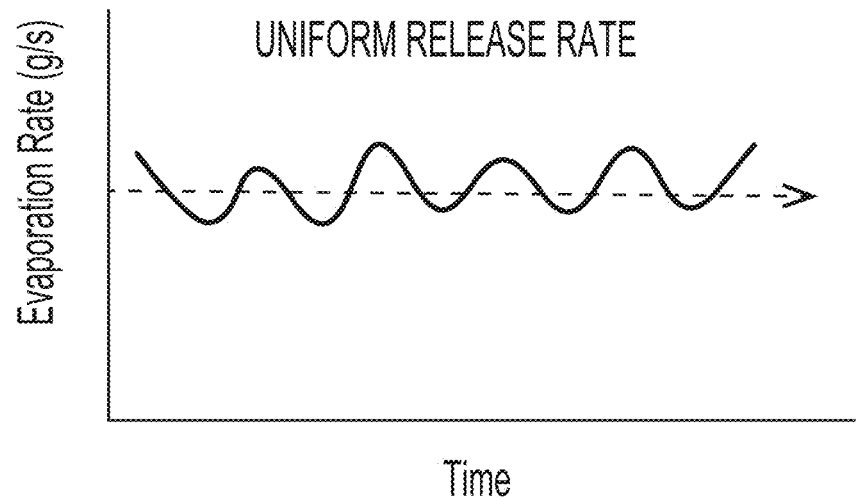
FIG. 14 is a plot of an exemplary uniform evaporation rate profile over time from an exemplary volatile composition dispenser.

A total emission program may generally be configured to achieve a uniform evaporation over time. Increasing the energy applied to the evaporative surface to yield an average evaporation rate over the life of the volatile composition in the reservoir. The energy may be increased by 3% to 500%, preferably 5% to 300%, more preferably 10% to 200%, more preferably 15% to 100%, over multiple intervals. The interval may include energy boosts every 1-20 days, preferably 1-15 days, more preferably 1-10 days, more preferably 1-7 days. A plot illustrative of a uniform evaporation rate is shown in FIG. 14.

Increasing Evaporation Rate

Figure 15:
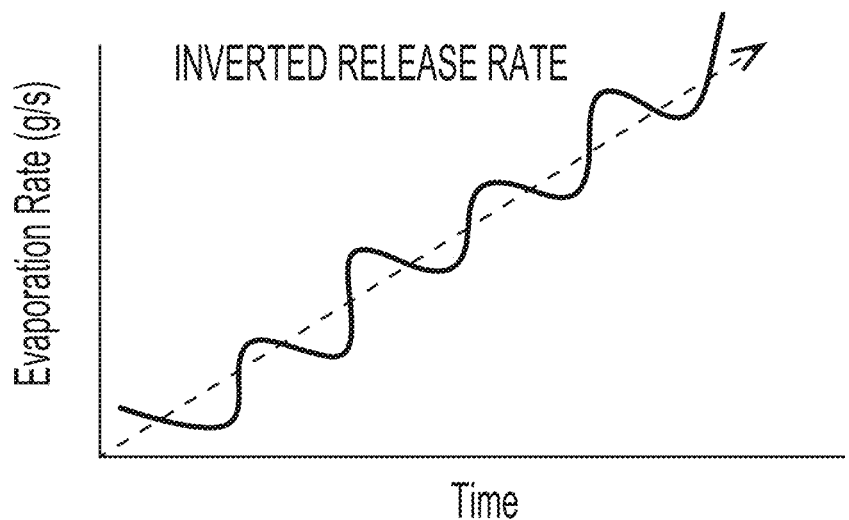
FIG. 15 is a plot of an exemplary increasing evaporation rate profile over time from an exemplary volatile composition dispenser.

Another method of operation includes increasing the energy applied to the evaporative surface over time to yield an average evaporation rate which is increasing on a regular basis. In order to increase the evaporation rate, the energy applied to the evaporative surface may increase by 3% to 500% on a regular interval. The regular interval may be increasing the energy every 1-20 days, preferably 1-15 days, more preferably 1-10 days, more preferably 1-7 days. Each newly established evaporation rate will be between 1% and 500% greater than the previous evaporation rate, more preferably between 5% and 400% than the previous evaporation rate, more preferably between 10% and 300% than the previous evaporation rate, more preferably between 10% and 250% of the previous evaporation rate, more preferably between 10% and 200% of the previous evaporation rate. A plot illustrating an increasing average evaporation rate is shown in FIG. 15.

Random Evaporation Rate

Figure 16:
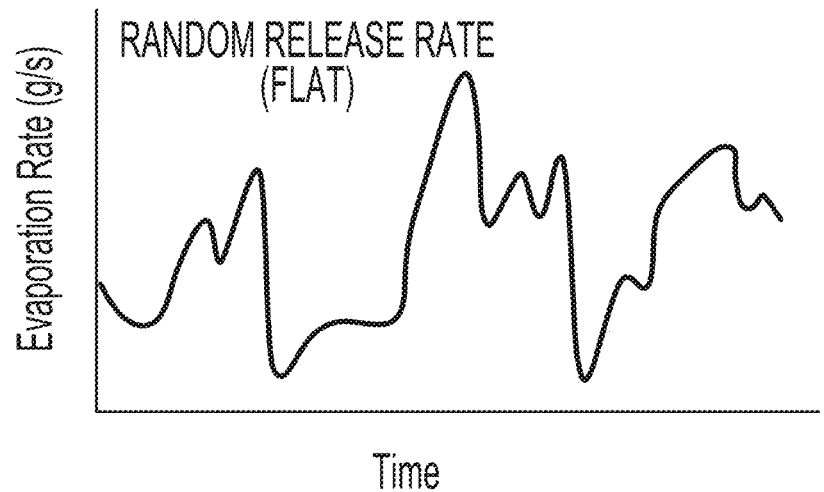
FIG. 16 is a plot of an exemplary random evaporation profile that on average is flat over time from an exemplary volatile composition dispenser.
Figure 17:
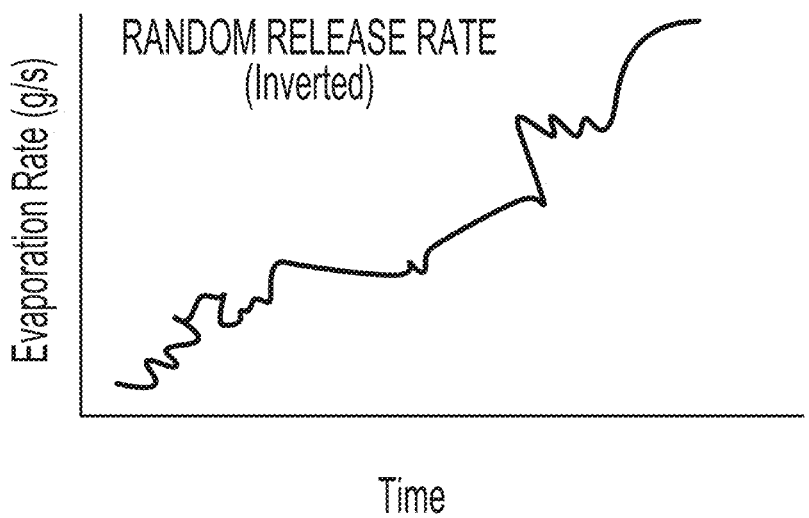
FIG. 17 is a plot of an exemplary random evaporation profile that on average increases over time from an exemplary volatile composition dispenser.

Another method of operation includes increasing or decreasing the energy applied to the evaporative surface by 3% to 500% on a regular or irregular interval to yield an average evaporation rate which is changing, either increasing or decreasing on a irregular basis. Each newly established evaporation rate will be between 1% and 500% greater or lesser than the previous evaporation rate, more preferably between 5% and 400% greater or lesser than the previous evaporation rate, more preferably between 10% and 300% greater or lesser than the previous evaporation rate, more preferably between 10% and 250% greater or lesser than the previous evaporation rate, more preferably between 10% and 200% greater or lesser than the previous evaporation rate. A plot of a random evaporation rate that is flat over the life of the volatile composition is shown in FIG. 16. A plot of a random evaporate rate that increases over the life of the volatile composition is shown in FIG. 17. Changing the evaporation rate over time may reduce the likelihood of a user becoming habituated to the volatile composition because a user is unable to predict when a discrete emission period will start or stop.

If the energy applied to the evaporative surface is increased over time, the method may include operating at a broad energy range. For example, over the life of the volatile composition contained in each reservoir, such as a period of weeks or months, for an evaporative assistance element configured as a heater, each evaporative assistance element may be configured to operate over a temperature range starting at about 25° C. and ending at about 120° C., more preferably starting at about 35° C. and ending at about 110° C., more preferably starting at about 40° C. and ending at about 110° C. more preferably starting at about 40° C. and ending at about 100° C., more preferably starting at about 45° C. and ending at about 100° C., more preferably starting at about 50° C. and ending at about 90° C.

Each evaporative assistance element could have a different temperature than any other evaporative assistance element in the system. Further these evaporative assistance element temperatures (for each evaporative assistance element) can change, either increase or decrease, each time a new discrete emission period is started.

In addition to or separate from changing the temperature of the evaporative assistance elements over the life of the volatile composition, other methods of alternating the evaporation rate may include increasing or decreasing the surface area of the delivery engine or evaporative surface exposed to the evaporative assistance element, and/or increasing or decreasing airflow to the delivery engine or evaporative surface. Adjustment of temperature, air flow, and surface area may be used independently or in parallel to control the evaporation rate of the volatile composition from the delivery engine or evaporative surface.

A total emission program for the volatile composition dispenser may include one or more methods, including varying energy, gap periods, random emission periods, and or simultaneous emission with one or more evaporative surfaces and one or more evaporative assistance elements. Varying energy, gap periods, random emission periods and/or simultaneous emission periods may result in a method that increasing user noticeability of the volatile composition in the space and/or decreases the likelihood that the user will become habituated to the one or more volatile compositions.

Gap Periods

The total emission program may include gap periods where all evaporative assistance elements of a volatile composition dispenser are turned OFF ("gap periods"). By introducing gap periods, the noticeability of the volatile composition in the space declines so that a user is less likely to be become habituated to the volatile composition.

Figure 18:
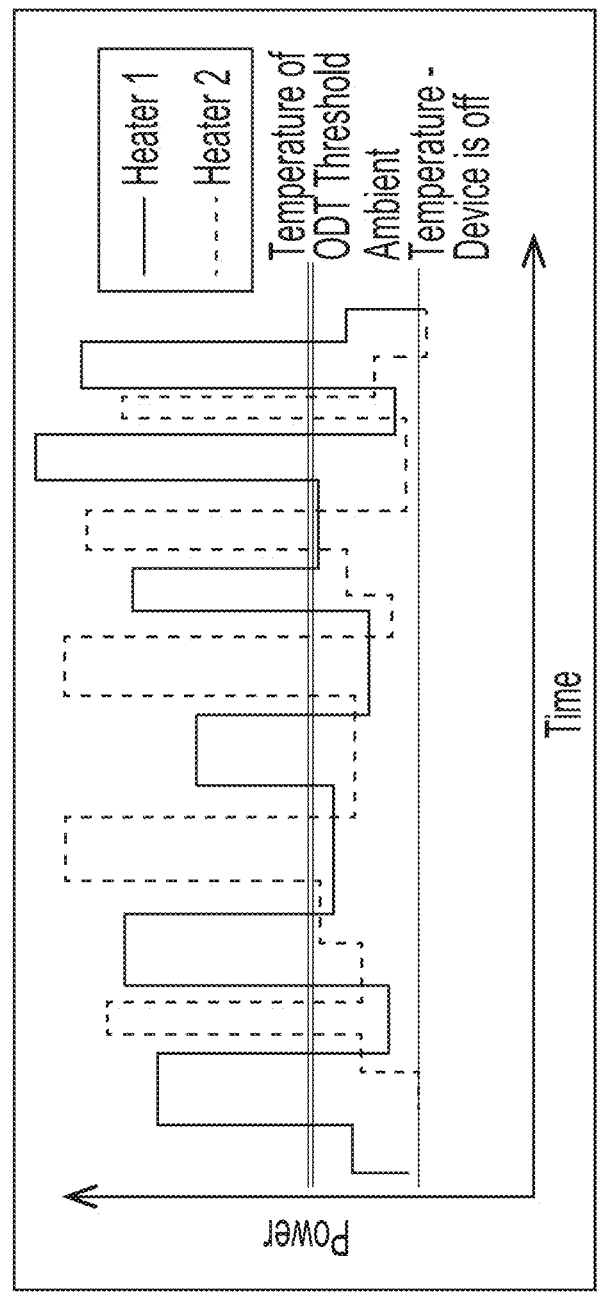
FIG. 18 is a plot of an exemplary energy profile of two heaters of a volatile composition dispenser that reduces the heater temperature such that evaporation is below the odor detection threshold of the volatile composition from an exemplary volatile composition dispenser.

Another method that may be used to achieve comparable results is to decrease the energy of the evaporative assistance element periodically such that the energy provided to the evaporative surface is below that which is necessary to evaporate the volatile composition at a sufficient level for the odor detection threshold ("ODT") of the volatile composition. The lowered evaporation rate and operation at sub-ODT levels provides a break from sensory stimulus, thus enabling enhanced noticeability when the stimulus is reintroduced. This operation also maintains the evaporative surface at a heightened state above ambient conditions enabling faster response time and/or less energy in order to return to steady-state upon the initiation of the next cycle phase. An example of operating at lowered release instead of turning off the evaporative assistance element is shown in FIG. 18.

Operating below the ODT of a volatile composition may translate to operating the evaporative assistance element at less than 30% of maximum power output, or less than 25% of maximum power output, or less than 20% of maximum power output, or less than 15% of maximum power output, or less than 10% of maximum power output.

There are many difference approaches for programming the evaporative assistance elements, such as heaters and fans, to operate in the various configurations discussed above. As a non-limiting example, where a volatile composition dispenser includes two evaporative assistance elements in the form of heaters, Heater A and Heater B, Heater B OFF time is equal to the ON time of Heater A operation and occurring either in parallel (e.g., Heater B is simultaneously OFF while Heater A is operating) or in series (e.g., Heater A is ON for 30 mins and then Heater B is OFF for 30 mins). The OFF time of each heater may be in the time period of 0 mins to 48 hours, preferably 5 mins to 24 hours, more preferably 10 mins to 24 hours. Another approach to programming the OFF time of the evaporative assistance elements may be defined as follows:

OFF TIME of Heater B (or any additional heater or evaporation assistance element,
such as Heater C, Heater D, etc, etc.)=D1+A1+D2,
Where:
A1=ON time of Heater A;
D1=deprivation factor ranging between 0 mins and the maximum operation time of Heater A (e.g., if Heater A is ON for 300 mins, the period of D1=0 mins to 300 mins); and
D2=a deprivation factor selected from a "pick list" of times (1 mins, 2 mins . . . 1440 mins). D2 may be predefined, picked from an array, randomly selected from a "pick list" or selected via a random number generator.

An exemplary program for a volatile composition dispenser may be defined as follows: Heater A turns ON and heats up for 60 minutes, while Heater A is on, Heater B is off the entire time (in parallel operation), Heater A then turns OFF and Heater B turns ON and operates for the same amount of time that Heater A operated (While Heater B is ON, heater A is OFF). Heater B then turns OFF. Both Heaters A and B remain OFF for a period of time of 0, 5, 10 or 15 minutes, for example. At this point the next heater (either Heater A, or a subsequent Heater C for example) is activated. The cycle continues until the end of the program is reached (Program cycle is defined as 60 days, for example). An example of Heater A=60 mins ON, Heater B=60 mins OFF, rest for 10 mins is below:

Heater A: On Time=60 mins
D1=60 mins
D2=Software picks random number from picklist "P1" {P1 is selected from either A-G, where A=0 mins, B=5 mins, C=10 mins, D=15 mins, E=20 mins, F=25 mins, G=30 mins.
Heater B OFF time=60+60+P1.

The programming description could be applied to any form of an evaporative assistance element, such as a heater or fan, for example. The programming could also be used in a volatile composition dispenser having a heater as one evaporative assistance element and a fan as a second evaporative assistance element.

Simultaneous Operation

The total emission program may include simultaneously operating the one or more evaporative assistance elements. The evaporative assistance elements can be operated simultaneously at a plurality of energy levels to create new volatile composition experiences that are more noticeable. By combining multiple volatile compositions and varying the evaporation rates of said volatile compositions, it is possible to create continually changing experiences (both in terms of intensity and in character) that combat both habituation. Having a plurality of volatile compositions over time allows for a unique and ever-changing stimulus that may always be noticeable. Operating a plurality of volatile composition simultaneously may also enable higher evaporation rates than are achievable by utilizing a single volatile composition while conserving total system volatile composition amounts. The evaporative assistance elements, if operated simultaneously, can operate simultaneously for just a portion of operation of each evaporative assistance element. For example, one evaporative surface element may run on at one time, followed by a period where the evaporative assistance element may run simultaneously with one or more of the other evaporative assistance elements, optionally followed by a period where the first evaporative assistance element to run may be turned OFF and the one or more other evaporative assistance element(s) may run on its own.

While in simultaneous operation (i.e., 2 or more evaporative assistance elements, heaters for example, running at the same time) the evaporative surface temperature, wick temperature for example, of the simultaneously operating evaporative surfaces will be 10% to 100% ("Temp %") of the evaporative surface temperature of the primary operating evaporative surface (Primary operating evaporative surface is defined as the evaporative which started operation first or, if all evaporative surfaces start their heating cycle at the same time) the lower numbered evaporative surface. The Temp % of simultaneously operating evaporative surfaces may be predefined, picked from an array, randomly selected from a "pick list" or selected via a random number generator operating within these predefined boundaries of 10% to 100%:
- Example #1—Wick 2 starts 10 minutes prior to Wick 1, the temperature of Wick 1=(0.10 to 1.00)*MaxProgrammedTempWICK2
- Example #2—Wick 1 and Wick 2 start simultaneously. Wick 1 is programmed to reach a MAX temp of 80 C. The temperature of Wick 2=(0.10 to 1.00)*MaxProgrammedTempWICK1.
- Example #3—Wick 3 has been operating for 25 minutes in a 30 minute cycle (with a MAX temp of 90° C.) when Wick 1 and Wick 2 are started simultaneously (5 min simultaneous overlap of all three heaters):
  - Primary wick is Wick 3 with a MAX temp of 90° C.
  - The software has determined the wick temp of simultaneously operating wicks will be 65% of the primary wick (0.65*90C=58.5C)
  - Wicks 1 and 2 are simultaneously operating wicks in this scenario
  - Volatile composition dispenser operation is as follows:
    - Heater 3 (example evaporative assistance element) operates for 25 minutes.
    - Heaters 1 and 2 turn on 25 minutes into the operation of Heater 3.
    - Heaters 3, 1 & 2 operate simultaneously for 5 mins-Heater3 MAX temp=90° C., Heater 1 & Heater 2 MAX temp=58.5° C.

While in simultaneous operation (i.e. 2 or more heaters running at the same time) the wick operation time ("ON time") of any simultaneously operating wicks (see temp description above for definitions of primary/secondary wicks) is a period of time SOT ("Simultaneous Operation Time") ranging from as low as 1 minute to as long as such point in time as the primary wick operation time has ended.
- Example #4—(Volatile composition dispenser comprising two wicks as two evaporative surfaces): Wick 1 has been operating for 15 minutes of a 60 minute cycle. Wick 2 (programmed for 90 minutes) enters simultaneous operation at the 15-minute mark of the primary wick (Wick 1). Wicks 1 and 2 operate simultaneously for the next 45 mins (Simultaneous Operation Time), completing the cycle of wick 1. Wick 1 then turns off, ending Simultaneous Operation Time. Wick 2 continues to operate for 45 more minutes in solo operation, completing the 90-minute cycle of wick 2.
- Example #5—(Volatile composition dispenser comprising three wicks as three evaporative surfaces): Wick 2 has been operating for 15 minutes of a 60-minute cycle. Wick 3 (programmed for 90 minutes) enters simultaneous operation at the 15-minute mark of the primary wick (Wick 2). Wicks 2 and 3 operate simultaneously for the next 40 mins (Simultaneous Operation Time). Wick 1 (Programmed for 75 mins) turns on at this point (55 minutes into the cycle of Wick 2 and 40 minutes into the cycle of Wick 3) and Wicks 1, 2 and 3 operate in simultaneous operation mode for 5 minutes, ending the simultaneous operation for Wick 2. Wicks 1 and 3 continue in simultaneous mode for 45 minutes, ending the simultaneous mode for Wick 3 (end of 90-minute cycle). Wick 1 continues to operate for 25 more minutes in solo operation, completing the 75-minute cycle of Wick 1.

Figure 19:
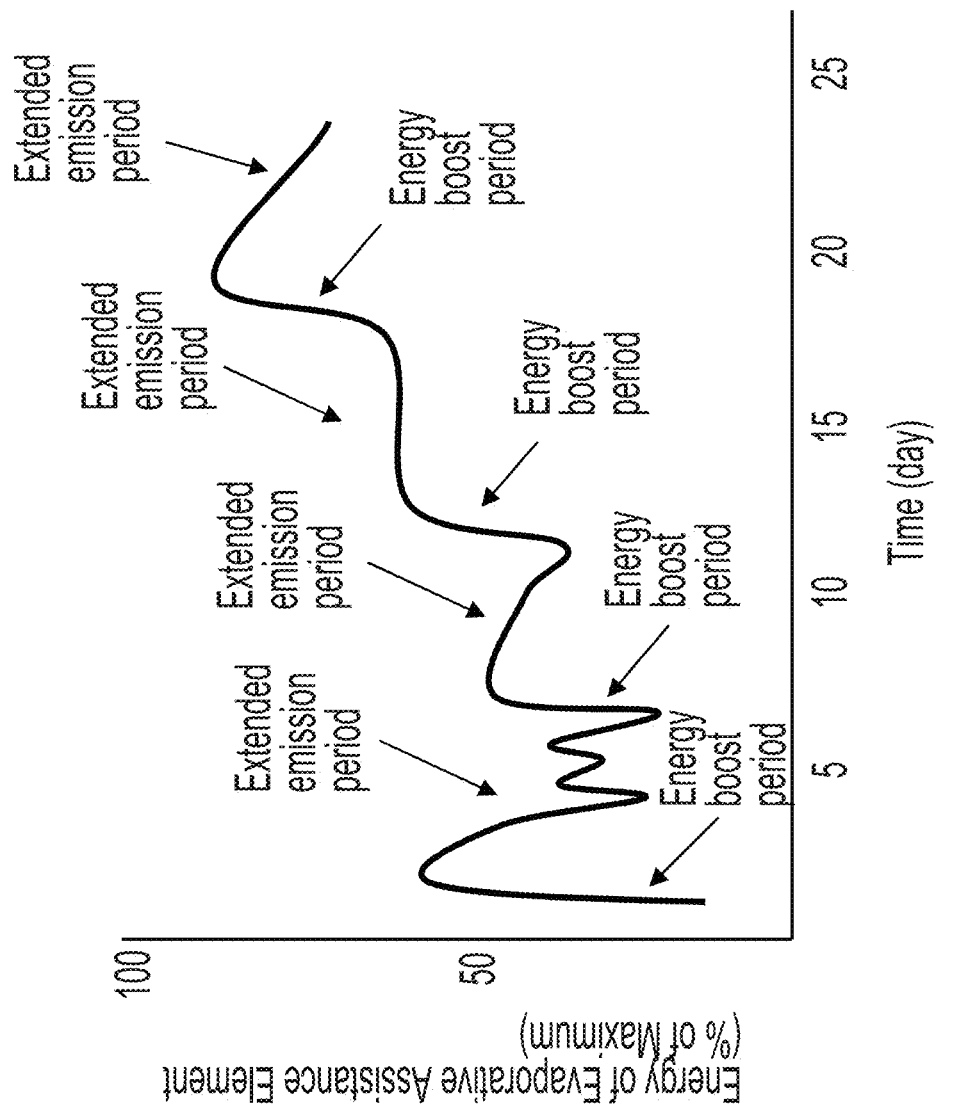
FIG. 19 is a plot of an exemplary total emission program for an evaporative assistance element of the present invention.

FIG. 19 illustrates another exemplary total emission program of the present invention having a plurality of energy boost periods separated by extended emission periods of lower or maintained energy.

Method of Determining the ODT of a Volatile Composition

ODTs may be determined using a commercial GC equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical GC parameters for determining ODTs are listed below. The test is conducted according to the guidelines associated with the equipment.

Equipment

GC: 5890 Series with FID detector (Agilent Technologies, Ind., Palo Alto, California, USA);
7673 Autosampler (Agilent Technologies, Ind., Palo Alto, California, USA);
Column: DB-1 (Agilent Technologies, Ind., Palo Alto, California, USA)
Length 30 meters ID 0.25 mm film thickness 1 micron (a polymer layer on the inner wall of the capillary tubing, which provide selective partitioning for separations to occur).

Method Parameters

Split Injection: 17/1 split ratio;
Autosampler: 1.13 microliters per injection;
Column Flow: 1.10 mL/minute;
Air Flow: 345 mL/minute;
Inlet Temp. 245° C.;
Detector Temp. 285° C.

Temperature Information

Initial Temperature: 50° C.;
Rate: 5C/minute;
Final Temperature: 280° C.;
Final Time: 6 minutes;
Leading assumptions: (i) 12 seconds per sniff
  (ii) GC air adds to sample dilution.

Method To Determine The Daily Average Evaporation Rate

1. Insert the cartridge or reservoir containing the volatile composition into the housing of the volatile composition dispenser to complete the assembly of the entire volatile composition dispenser. Ensure that the cartridge or reservoir is fully inserted into the housing by grasping the cartridge or reservoir and gently tugging to confirm a secure engagement with the housing.

2. Place the entire volatile composition dispenser (housing+cartridge/reservoir) onto an analytical balance.

3. Using the analytical balance, measure and record the total weight of the volatile composition dispenser to two decimal places (e.g. 100.00 g).

4. Adjust the volatile composition dispenser intensity to the desired test condition (e.g.—HIGH, MEDIUM, LOW)

5. Activate or power on the volatile composition dispenser (e.g. for a pluggable volatile composition dispenser, plug the volatile composition dispenser into the appropriate voltage) and record the time (hours and minutes).

6. Remove the volatile composition dispenser from operation by deactivating, turning off, unplugging, etc. after at least 24 hours has elapsed. Record the time (hour and minutes) and total volatile composition dispenser weight.

7. Once the system weight and time have been recorded, return the volatile composition dispenser to normal operation. Steps 6 and 7 should take no more than 15 minutes.

8. Repeat steps 5-7 as often as desired in regular intervals of ~24 hours or greater.

Evaporation Rate Calculation:

Evaporation rate is calculated per the following formula:

$$\frac{(\text{Weight, gms}_1 - \text{Weight, gms}_2)}{\text{Time in hours}} \times \frac{1000 \text{ mg}}{1 \text{ g}} = \text{mg/hr},$$

*1000 is the factor to convert g to milligrams

Consumer Study #1

Figure 20:
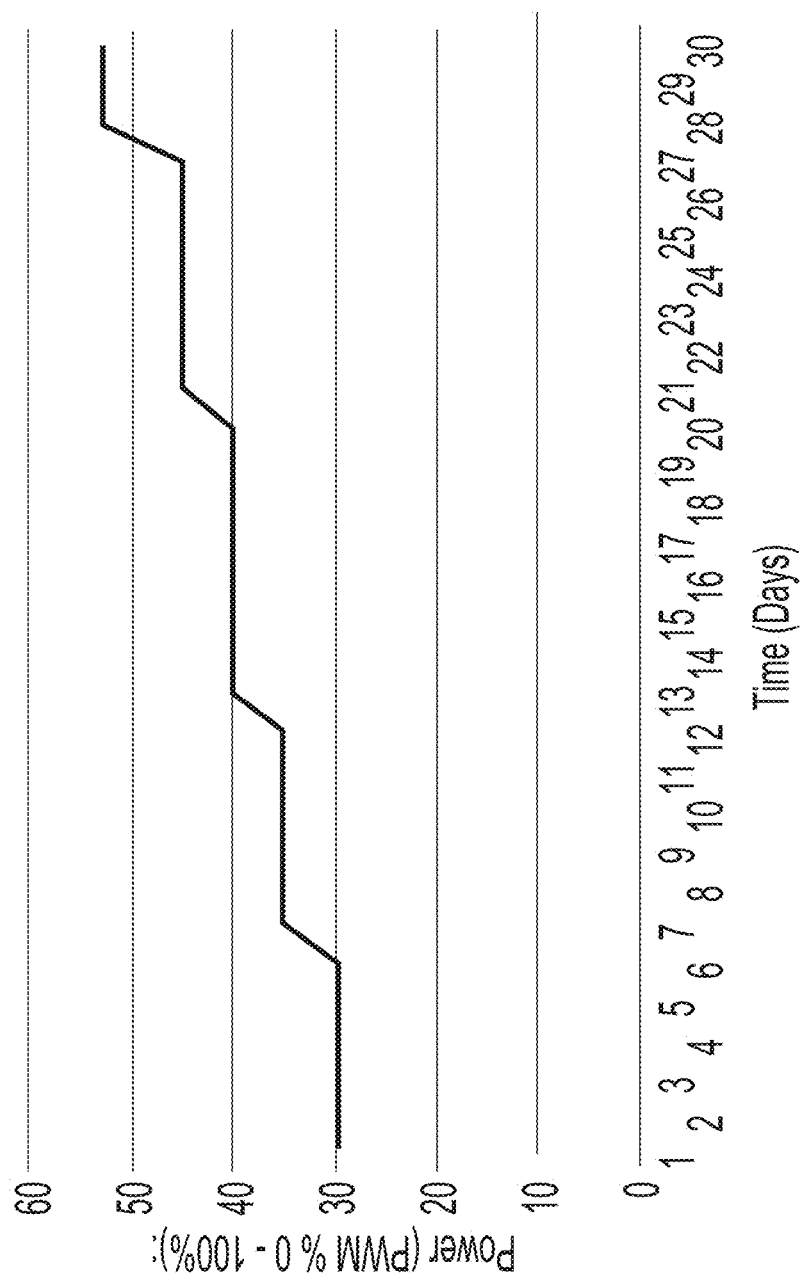
FIG. 20 is a plot of a comparative total emission program of Consumer Study #1.

Volatile Composition Dispensers tested:

Product A: A volatile composition dispenser having two cartridges, an evaporative surface for each cartridge, and an evaporative assistance element in the form of a heater for each evaporative surface such as illustrated in FIGS. 1-3. The total emission program for Product A is illustrated in FIG. 20.

Product B: The same volatile composition dispenser as Product A was used in Product B. The total emission program for Product B is illustrated in FIG. 8.

Comparative Product 1 is a commercially available volatile composition dispenser having two cartridges, an evaporative surface for each cartridge, and an evaporative assistance element in the form of a heater for each evaporative surface.

Comparative Product 2 is a commercially available volatile composition dispenser having a single cartridge, single evaporative surface, and an evaporative assistance element in the form of a heater.

Consumer panelists ("panelists") were recruited that currently use scented oil products of different brands.

Panel 1 included 9 panelists; 5 consumers ("Group 1") that currently use one brand of commercially available scented oil product (hereinafter "Comparative Product 1"); and 4 consumers ("Group 2") that currently use a different brand of commercially available scented oil product (hereinafter "Comparative Product 2"). Panelists were placed with Product A product to use in their home for 4 weeks. At the end of the 4-week period, consumers were interviewed by trained researchers in their homes. Product A was retrieved, and the Comparative Product (Comparative Product 1 for Group 1 panelists and Comparative Product 2 for Group 2 panelists) was placed to use for 4 weeks. At the end of the second 4-week period, panelists were interviewed by trained researchers in their homes. The Comparative Products were retrieved, and Product B was placed for a 4-week period. At the end of the third 4-week period, panelists were again interviewed in their homes by trained researchers. Panelists were asked a series of questions comparing the 3 products they had used. The results are below in Table 2.

TABLE 2

Consumer Panel #1 Product Evaluation

| Attribute | Product A | Comparative Product 1 or 2 | Product B | No preference |
|---|---|---|---|---|
| Room Fill | X | X | XXXXX | XX |
| Scent Character | X | XXXXX | XX | X |
| Scent Reach | X | XXX | XXXX | X |
| Scent Consistency | XX | | XXXXXXX | |
| Scent Longevity | | XXX | XXXXXX | |

Group 1 Forced Purchased Choice; zero panelists picked Product A; five panelists picked the respective Comparative Product (however two of the five said it was the scent that made them choose the Comparative Product and they would prefer a volatile composition dispenser having the function of Product B with the scent of the Comparative Product); four panelists picked product B. It was surprising that consumers did not prefer Product A over the Comparative Product because Product A had energy boosts with increasing energy over time to deliver a more consistent evaporation rate than the Comparative Product. However, it was found with the Comparative Product and Product B that consumers demand a minimum level of noticeability of the volatile composition at the beginning of the total emission program, and Product A did not provide a high enough evaporation rate to achieve that minimum level of noticeability. So, even though Product A had a higher evaporation rate over the total emission program than the Comparative Product, consumers preferred the Comparative Product or Product B over Product A. Product B met the consumers' needs for room fill, scent reach, scent consistency, and scent longevity more than Product A or the Comparative Product because Product be provided the initial energy boost in combination with the increased energy over time.

Consumer Study #2

Volatile Composition Dispensers tested:

Product C: The same volatile composition dispenser as Product A was used in Product C. The program for Product C is illustrated in FIG. 11.

Comparative Product 1 is the same as Comparative Product 1 in Consumer Panel #1.

Comparative Product 2 is the same as Comparative Product 2 in Consumer Panel #2.

Panel 2 was also recruited using the same recruitment criteria as Panel 1.

Panel 2 included 10 panelists; 4 current users of Comparative Product 1 and 6 current users of Comparative Product 2. Panelists were placed with Product C product to use in their home for 4 weeks. At the end of the 4-week period, panelists were interviewed by trained researchers in their homes. Product C was retrieved, and the Comparative Product (Comparative Product 1 for Group 1 panelists and Comparative Product 2 for Group 2 panelists) was placed to use for 4 weeks. At the end of the second 4-week period, panelists were interviewed by trained researchers in their homes. Panelists were asked a series of questions comparing the two products they had used. The results are below in Table 3.

TABLE 3

Consumer Panel #2 Product Evaluation

| Attribute | Product C | Comparative Product 1 or 2 | No preference |
|---|---|---|---|
| Room Fill | XXXXXXXXX | X | |
| Scent Character | XXXXX | XXXX | X |
| Scent Reach | XXXXXXXX | XX | |
| Scent Consistency | XXXXXXXX | XX | |
| Scent Longevity | XXXXXXXXX | X | |

Group 2 forced purchase choice: eight panelists picked Product C; two panelists picked the respective Comparative Product, however one of the two said it was the scent of the respective Comparative Product with the performance of Product C. The panelists preferred Product C, which had an initial energy boost and subsequent energy boosts that were followed by periods of extended emission periods of decreasing energy, to the Comparative Product.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

It should be understood that every maximum numerical limitation given throughout this specification will include every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of dispensing a volatile composition, the method comprising the steps of:

providing a volatile composition dispenser, the volatile composition dispenser comprising:
a cartridge comprising a reservoir for containing the volatile composition,
a delivery engine in fluid communication with the reservoir,
an evaporative surface in fluid communication with the delivery engine,
an evaporative assistance element adjacent at least a portion of the evaporative surface, wherein the evaporative assistance element defines a maximum power output, and
a microprocessor configured to control a temperature of the evaporative assistance element by: starting a total emission program for the volatile composition dispenser at time zero when the volatile composition dispenser is first powered and the cartridge is new or refilled to be full of the volatile composition, wherein the total emission program comprises a plurality of discrete emission periods;
initiating a first discrete emission period by increasing energy to the evaporative assistance element to a first boost energy in a first energy boost period, wherein the first boost energy is at least 75 percent greater than an energy immediately before the increase to the first boost energy;
decreasing energy applied by the evaporative assistance element to a first extended energy;
operating the evaporative assistance element at the first extended energy over a first extended energy period, wherein the first extended energy period includes a period of maintained energy level, and wherein the first extended energy period is greater than the first energy boost period;
initiating a second discrete emission period by increasing energy applied by the evaporative assistance element to a second boost energy in a second energy boost period, wherein the second boost energy is at least 75 percent greater than an energy immediately before the increase to the second boost energy;
decreasing energy applied by the evaporative assistance element to a second extended energy; and
operating the evaporative assistance element at the second extended energy over a second extended energy period, wherein the second extended energy period includes a period of maintained energy level, and wherein the second extended energy period is greater than the second energy boost period.

2. The method of claim 1, wherein the first boost energy and the second boost energy are different.

3. The method of claim 1, further comprising the steps of initiating a third discrete emission period by increasing energy applied by the evaporative assistance element to a third boost energy in a third energy boost period, wherein the third boost energy is at least 75 percent greater than an energy immediately before the increase to the third boost energy;
decreasing energy applied by the evaporative assistance element to a third extended energy; and
operating the evaporative assistance element at the third extended energy over a third extended energy period, wherein the third extended energy period includes a period of maintained energy level, and wherein the third extended energy period is greater than the third energy boost period.

4. The method of claim 3, wherein the third boost energy is different than the second boost energy.

5. The method of claim 4, wherein the third boost energy is different than the first boost energy.

6. The method of claim 3, further comprising the step of operating the evaporative assistance element for a gap period between the first energy boost period, the second energy boost period and the third energy boost period.

7. The method of claim 6, further comprising the step of operating the evaporative assistance element for a gap period between the first energy boost period and the second energy boost period and a gap period between the second energy boost period and the third energy boost period.

8. The method of claim 7, wherein each of first discrete emission period, the second discrete emission period, and the third discrete emission period individually lasts from about 30 minutes to about 4 hours.

9. The method of claim 8, wherein each of the first discrete emission period, the second discrete emission period, and the third discrete emission period individually last from about 30 minutes to about 1 hour.

10. A method of dispensing a volatile composition, the method comprising the steps of:
providing a volatile composition dispenser, the volatile composition dispenser comprising a cartridge comprising a reservoir for containing the volatile composition, a delivery engine in fluid communication with the reservoir, an evaporative surface in fluid communication with the delivery engine, an evaporative assistance element adjacent at least a portion of the evaporative surface, wherein the evaporative assistance element defines a maximum power output, and a microprocessor configured to control a temperature of the evaporative assistance element by:
starting a total emission program for the volatile composition dispenser at time zero when the volatile composition dispenser is first powered and the cartridge is new or refilled to be full of the volatile composition, wherein the total emission program comprises a plurality of discrete emission periods;
initiating a first discrete emission period by increasing energy applied by the evaporative assistance element to a first boost energy in a first energy boost period, wherein the first boost energy is at least 75 percent greater than an energy immediately before the increase to the first boost energy;
decreasing energy applied by the evaporative assistance element;
initiating a second discrete emission period by increasing energy applied by the evaporative assistance element to a second boost energy in a second energy boost period, wherein the second boost energy is at least 75 percent greater than an energy immediately before the increase to the second boost energy, and wherein the second boost energy is greater than the first boost energy;
decreasing energy applied by the evaporative assistance element to a second extended energy; and
operating the evaporative assistance element at the second extended energy over a second extended energy period, wherein the second extended energy period includes a period of maintained energy level, and wherein the second extended energy period is greater than the second energy boost period.

11. The method of claim 10, further comprising the steps of initiating a third discrete emission period by increasing energy applied by the evaporative assistance element to a third boost energy in a third energy boost period, wherein the third boost energy is at least 75 percent greater than an energy immediately before the increase to the third boost energy;
decreasing energy applied by the evaporative assistance element to a third extended energy; and
operating the evaporative assistance element at the third extended energy over a third extended energy period, wherein the third extended energy period includes a period of maintained energy level, and wherein the third extended energy period is greater than the third energy boost period.

12. The method of claim 11, wherein the third boost energy is different than the second boost energy.

13. The method of claim 11, wherein the third boost energy is different than the first boost energy.

14. The method of claim 13, further comprising the step of operating the evaporative assistance element for a gap period between the first energy boost period and the second energy boost period and between the second energy boost period and the third energy boost period.

15. The method of claim 14, further comprising the step of operating the evaporative assistance element for a gap period between the first energy boost period and the second energy boost period and a gap period between the second energy boost period and the third energy boost period.

16. The method of claim 15, wherein each of the first discrete emission period, the second discrete emission period, and the third discrete emission period individually lasts from about 30 minutes to about 4 hours.

17. The method of claim 16, wherein each of the first discrete emission period, the second discrete emission period, and the third discrete emission period individually last from about 30 minutes to about 1 hour.

18. The method of claim 17, wherein the first boost energy and the second boost energy are within 10 percent of one another.

19. A method of dispensing a volatile composition, the method comprising the steps of:
providing a volatile composition dispenser, the volatile composition dispenser comprising a cartridge comprising a reservoir for containing the volatile composition, a delivery engine in fluid communication with the reservoir, an evaporative surface in fluid communication with the delivery engine, an evaporative assistance element adjacent at least a portion of the evaporative surface, wherein the evaporative assistance element defines a maximum power output, and a microprocessor configured to control a temperature of the evaporative assistance element by:
starting a total emission program for the volatile composition dispenser at time zero when the volatile composition dispenser is first powered and the cartridge is new or refilled to be full of the volatile composition, wherein the total emission program comprises a plurality of discrete emission periods;
initiating a first discrete emission period by increasing the energy applied by the evaporative assistance element to a first boost energy in a first energy boost period to achieve a first boost temperature, wherein the first boost temperature is greater than a temperature immediately before the increase to the first boost energy, and wherein the first boost temperature is from between about 40° C. and 80° C.;
decreasing the energy applied by the evaporative assistance element;
initiating a second discrete emission period by increasing the energy applied by the evaporative assistance element to a second boost energy in a second energy boost period to achieve a second boost temperature, wherein the second boost temperature is greater than a temperature immediately before the increase to the second boost energy, and wherein the second boost temperature is from between about 50° C. and 90° C., and wherein the second boost temperature is greater than the first boost temperature;

decreasing the energy applied by the evaporative assistance element to a second extended energy; and operating the evaporative assistance element at the second extended energy over a second extended energy period, wherein the second extended energy period includes a period of maintained energy level, and wherein the second extended energy period is greater than the second energy boost period.

20. The method of claim 19, further comprising the steps of initiating a third discrete emission period by increasing energy applied by the evaporative assistance element to a third boost energy in a third energy boost period to achieve a third boost temperature, wherein the third boost temperature is greater than a temperature immediately before the increase to the third boost energy, and wherein the third boost temperature is from between about 60° C. and 100° C., and wherein the third boost temperature is greater than the first boost temperature;

decreasing energy applied by the evaporative assistance element to a third extended energy; and operating the evaporative assistance element at the third extended energy over a third extended energy period, wherein the third extended energy period includes a period of maintained energy level, and wherein the third extended energy period is greater than the third energy boost period.

21. The method of claim 20, wherein the third boost energy is different than the second boost energy.

22. The method of claim 20, wherein the third boost energy is different than the first boost energy.

23. The method of claim 22, further comprising the step of operating the evaporative assistance element for a gap period between the first energy boost period and the second energy boost period and between the second energy boost period and the third energy boost period.

24. The method of claim 23, further comprising the step of operating the evaporative assistance element for a gap period between the first energy boost period and the second energy boost period and a gap period between the second energy boost period and the third energy boost period.

25. The method of claim 24, wherein each of the first discrete emission period, the second discrete emission period, and the third discrete emission period individually lasts from about 30 minutes to about 4 hours.

26. The method of claim 25, wherein each of the first discrete emission period, the second discrete emission period, and the third discrete emission period individually last from about 30 minutes to about 1 hour.

* * * * *